US008637024B2

(12) United States Patent
Ho et al.

(10) Patent No.: US 8,637,024 B2
(45) Date of Patent: Jan. 28, 2014

(54) FUSION ANTIBODIES FOR HIV THERAPY

(75) Inventors: David Ho, New York, NY (US); Yaoxing Huang, New York, NY (US); Craig Pace, New York, NY (US); Ruijiang Song, New York, NY (US); Qing Fang, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 13/294,652

(22) Filed: Nov. 11, 2011

(65) Prior Publication Data

US 2012/0121597 A1 May 17, 2012

Related U.S. Application Data

(60) Provisional application No. 61/413,178, filed on Nov. 12, 2010.

(51) Int. Cl.
*A61K 39/00* (2006.01)
*A61K 39/42* (2006.01)
*A61K 39/395* (2006.01)
*A61K 38/00* (2006.01)

(52) U.S. Cl.
USPC ............. 424/136.1; 424/160.1; 424/172.1; 514/1.1

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,225,539 A | 7/1993 | Winter |

FOREIGN PATENT DOCUMENTS

| JP | 7068276 B2 | 7/1995 |
| JP | 2004-518624 A | 6/2004 |

OTHER PUBLICATIONS

Briz et al., Journal of Antimicrobial Chemotherapy, 2006, 57:619-627.*
Lin et al., Entry Inhibitors in HIV Therapy, 2007, Edited by Jacqueline D. Reeves and Cynthia A. Derdeyn.*
McKnight et al., PNAS, 2003, 100(19):10581-10582.*
Jacobson, J.M. et al., "Safety, Pharmacokinetics, and Antiretroviral Activity of Multiple Doses of Ibalizumab (formerly TNX-355), an Anti-CD4 Monoclonal Antibody, in Human Immunodeficiency Virus Type 1-Infected Adults" Antimicrobial Agents and Chemotherapy (Nov. 17, 2008) pp. 450-457, vol. 53, No. 2.
Walker, L.M. et al., "Broad and Potent Neutralizing Antibodies from an African Donor Reveal a New HIV-1 Vaccine Target" Science (Oct. 9, 2009) pp. 285-289, vol. 326.
Chen, W. et al., "Human Domain Antibodies to Conserved Sterically Restricted Regions on gp120 as Exceptionally Potent Cross-Reacting HIV-1 Neutralizers" PNAS (Nov. 4, 2008) pp. 17121-17126, vol. 105, No. 44.
Zhou, T. et al., "Structural Basis for Broad and Potent Neutralization of HIV-1 Antibody VRC01" Science (Aug. 13, 2010) pp. 811-817, vol. 329.
Kamei, D.T. et al., "Quantitative Methods for Developing FC Mutants with Extended Half-Lives" Biotechnology and Bioengineering (Aug. 31, 2005) pp. 748-760, vol. 92, No. 6.
International Search Report dated May 2, 2012 issued in corresponding International Application No. PCT/US2011/060357.
Moore, J.P. et al., "The Entry of Entry Inhibitors: A Fusion of Science and Medicine" Proc Natl Acad Sci USA (2003), pp. 10598-10602, vol. 100, No. 19.
Huang, C. et al., "Structural Basis of Tyrosine Sulfation and VH-egne Usage in Antibodies that Recognize the HIV Type 1 Coreceptor-Binding Site on gp120" Proc Natl Acad Sci USA (2004) pp. 2706-2711, vol. 101, No. 9.
Labrijn, A. F. et al. "Access of Antibody Molecules to the Conserved Coreceptor Binding Site on Glycoprotein gp120 is Sterically Restricted on Primary Human Immunodefieincy Virus Type 1" J. Virol. (2003) pp. 10557-10565, vol. 77.
Kuritzkes, D.R. et al., Antiretroviral Activity of the Anti-CD4 Monoclonal Antibody TNX-355 in Patients Infected with HIV Type 1 J. Infect. Dis. (Jan. 15, 2004) pp. 286-291, vol. 189.
Burkly, L.C. et al., "Inhibition of HIV Infection by a Novel CD4 Domain 2-Specific Monoclonal Antibody" J. Immunol. (Sep. 1, 1992) pp. 1779-178, vol. 149, No. 5.
Jones, P.T. et al., "Replacing the Complementarity-Determining Regions in a Human Antibody with those from a Mouse" Nature (May 29, 1986) pp. 522-525, vol. 321.
Riechmann, L. et al., "Reshaping Human Antibodies for Therapy" Nature (Mar. 24, 1988) pp. 323-327, vol. 332.
Verhoeyen, M. et al., "Reshaping Human Antibodies: Grafting an Antilysozyme Activity" Science (1988) pp. 1534-1536, vol. 239.
Hessell, A.J. et al., "Fc Receptor but not Complement Binding is Important in Antibody Protection Against HIV" Nature (Sep. 6, 2007) pp. 101-104, vol. 449.
Ghetie, V. et al., "Transcytosis and Catabolism of Antibody" Immunol. Res. (2002) pp. 97-113, vol. 25, No. 2.
Roopenian, D.C. et al., "FcRn: the Neonatal Fc Receptor Comes of Age" Nat. Rev. Immunol. (Sep. 2007) pp. 715-725, vol. 7, No. 9.
Zalevsky, J. et al., "Enhanced Antibody Half-Life Improves in vivo Activity" Nat. Biotechnol. (Feb. 2010) pp. 157-159, vol. 28, No. 2.

(Continued)

*Primary Examiner* — Nicole Kinsey White
(74) *Attorney, Agent, or Firm* — Clark & Elbing LLP

(57) ABSTRACT

Disclosed herein are fusion antibodies created to provide both an antigen-binding site that targets the CD4 receptor and an antigen-binding site that targets the HIV envelope. The fusion antibodies disclosed herein provide improved potency and breadth against HIV as compared to monospecific antibodies, and additionally provide high barrier against viral resistance. Also disclosed are pharmaceutical formulations and therapeutic methods utilizing such fusion proteins.

29 Claims, 27 Drawing Sheets
(23 of 27 Drawing Sheet(s) Filed in Color)

(56) References Cited

OTHER PUBLICATIONS

Lagenaur, L.A. et al., "sCD4-17b Bifunctional Protein: Extremely Broad and Potent Neutralization of HIV-1 Env Pseudotyped Viruses from Genetically Diverse Primary Isolates" Retrovirology (2010) pp. 1-13, vol. 7, No. 11.

Schanzer, J. et al., "Development of Tertavalent Bispecific CCR5 Antibodies with Antiviral Activity Against CCR5 Monoclonal Antibody-Resistant HIV-1 Strains" Antimicrobial Agents and Chemotherapy (May 2011) pp. 2369-2378, vol. 55, No. 5.

Song et al., "Epitope Mapping of Ibalizumab, a Humanized Anti-CD4 Monoclonal Antibody with Anti-HIV-1 Activity in Infected Patients," *J. Virol.* 84:6935-6942 (2010).

\* cited by examiner

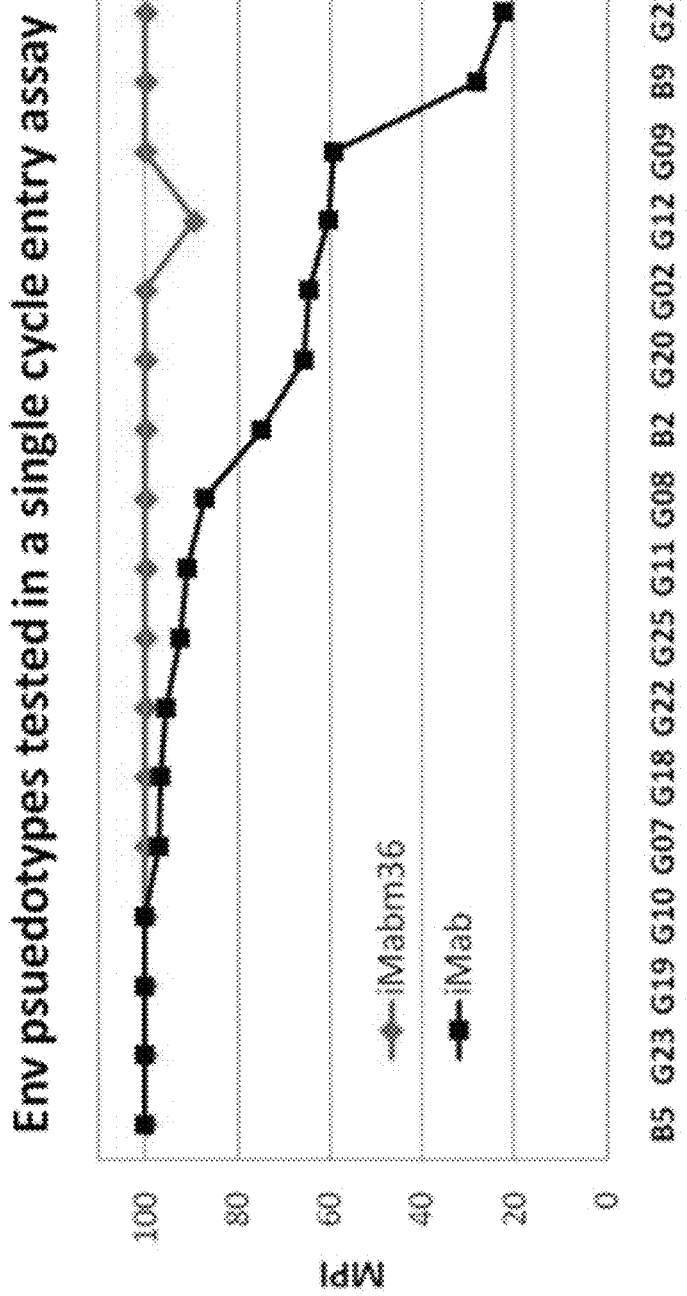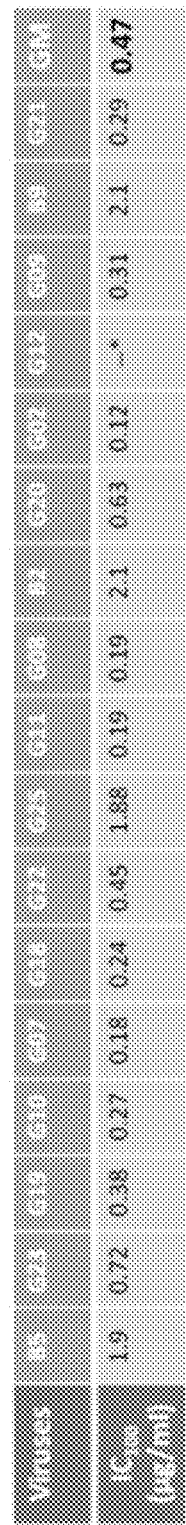
Figure 6

A

MEWSGVFMFL LSVTAGVHSQ VQLQQSGPEV VKPGASVKMS CKASGYTFTS YVIHWVRQKP

GQGLDWIGYI NPYNDGTDYD EKFKGKATLT SDTSTSTAYM ELSSLRSEDT AVYYCAREKD

NYATGAWFAY WGQGTLVTVS SASTKGPSVF PLAPSSKSTS GGTAALGCLV KDYFPEPVTV

SWNSGALTSG VHTFPAVLQS SGLYSLSSVV TVPSSSLGTQ TYICNVNHKP SNTKVDKKVE

PKSCDKTHTC PPCPAPEFEG GPSVFLFPPK PKDTLMISRT PEVTCVVVDV SHEDPEVKFN

WYVDGVEVHN AKTKPREEQY NSTYRVVSVL TVLHQDWLNG KEYKCKVSNK ALPASIEKTI

SKAKGQPREP QVYTLPPSRD ELTKNQVSLT CLVKGFYPSD IAVEWESNGQ PENNYKTTPP

VLDSDGSFFL YSKLTVDKSR WQQGNVFSCS VLHEALHSHY TQKSLSLSPG KLEGGGGSGG

GGSGGGGSGG VQLVQSGGGL VQPGGSLRLS CAASAFDFSD YEMSWVRQAP GKGLEWIGEI

NDSGNTIYNP SLKSRVTISR DNSKNTLYLQ MNTLRAEDTA IYYCAIYGGN SGGEYWGQGT LVTVSS*

B

MEWSGVFIFL LSVTAGVHSD IVMTQSPDSL AVSLGERVTM NCKSSQSLLY STNQKNYLAW

YQQKPGQSPK LLIYWASTRE SGVPDRFSGS GSGTDFTLTI SSVQAEDVAV YYCQQYYSYR

TFGGGTKLEI KRTVAAPSVF IFPPSDEQLK SGTASVVCLL NNFYPREAKV QWKVDNALQS

GNSQESVTEQ DSKDSTYSLS STLTLSKADY EKHKVYACEV THQGLSSPVT KSFNRGEC*

1          20
MEWSGVFMFL LSVTAGVHSQ RLVESGGGVV QPGSSLRLSC AASGFDFSRQ GMHWVRQAPG

QGLEWVAFIK YDGSEKYHAD SVWGRLSISR DNSKDTLYLQ MNSLRVEDTA TYFCVREAGG 158              176
PDYRNGYNYY DFYDGYYNTH YMDVWGKGTT VTVSSGLGS GGGGSGGGGS GGGGSQSALT

QPASVSGSPG QSITISCNGT SNDVGGYESV SWYQQHPGKA PKVVIYDVSK RPSGVSNRFS

288
GSKSGNTASL TISGLQAEDE GDYYCKSLTS TRRRVFGTGT KLTVLSGGGG SGGGGSGGGG

302
SQVQLQQSGP EVVRPGASVK MSCKASGYTF TSYVIHWVRQ KPGQGLDWIG YINPYNDGTD

YDEKFKGKAT LTSDTSTSTA YMELSSLRSE DTAVYYCARE KDNYATGAWF AYWGQGTLVT

424
VSSASTKGPS VFPLAPSSKS TSESTAALGC LVKDYFPEPV TVSWNSGSLT SGVHTFPAVL

QSSGLYSLSS VVTVPSSSLG TQTYVCNVNH KPSNTKVDKR VEIKTCGGGS KPPTCPPCPA

PEAAGGPSVF LFPPKPKDTL MISRTPEVTC VVVDVSQEDP EVKFNWYVNG AEVHHAQTKP

RETQYNSTYR VVSVLTVTHQ DWLNGKEYTC KVSNKALPAS IQKTISKDKG QPREPQVYTL

PPSREELTKN QVSLTCFVKG FYPSDIVVEW ESSGQPENTY KTTPPVLDSD GSYFLYSRLT

758
VDKSRWQQGN VFSCSVMHEA LHNHYTQKSL SVSPGK*

B

1          21
MRVPAQLLGL LLLWLPGARG DIVMTQSPDS LAVSLGERVT MNCKSSQSLL YSTNQKNYLA

WYQQKPGQSP KLLIYWASTR ESGVPDRFSG SGSGTDFTLT ISSVQAEDVA VYYCQQYYSY

134
RTFGGGTKLE IKRAAPSVFI FPPSDEQLKS GTASVVCLLN NFYPREAKVQ WKVDNALQSG

236
NSQESVTEQD SKDSTYSLSS TLTLSKADYE KHKVYACEVT HQGLSSPVTK SFNRGE*

1
QVQLVQSGGQ MKKPGESMRI SCRASGYEFI DCTLNWIRLA PGKRPEWMGW LKPRGGAVNY

ARPLQGRVTM TRDVYSDTAF LELRSLTVDD TAVYFCTRGK NCDYNWDFEH WGRGTPVIVS
        122             142
SGGGGSGGGG SGGGGSGGGG SEIVLTQSPG TLSLSPGETA IISCRTSQYG SLAWYQQRPG

QAPRLVIYSG STRAAGIPDR FSGSRWGPDY NLTSNLESG DFGVYYCQQY EFFGQGTKVQ
        246             256
VDKRGGGGS GGGGSGGGGS GGGGSQVQLQ QSGPEVVKPG ASVKMSCKAS GYTFTSYVIH

WVRQKPGQGL DWIGYINPYN DGTDYDEKFK GKATLTSDTS TSTAYMELSS LRSEDTAVYY
                                    388
CAREKDNYAI GAWFAYWGQG TLVTVSSAST KGPSVFPLAP SSKSTSESTA ALGCLVKDYF

PEPVTVSWNS GSLTSGVHTF PAVLQSSGLY SLSSVVTVPS SSLGTQTYIC NVNHKPSNTK

VDKRVEIKTC GGGSKPPTCP PCPAPEAAGG PSVFLFPPKP KDTLMISRTP EVTCVVVDVS

QEDPDVKFNW YVNGAEVHHA QTKPRETQYN STYRVVSVLT VTHQDWLNGK EYTCKVSNKA

LPASIQKTIS KDKGQPREPQ VYTLPPSREE LTKNQVSLTC PVKGFYPSDI VVEWESSGQP
                                                              722
ENTYKTTPPV LDSDGSYFLY SKLTVDKSRW QQGNVFSCSV MHEALHNHYT QKSLSVSPGK*

B

1                  21
MRVPAQLLGL LLLWLPGARG DIVMTQSPDS LAVSLGERVT MNCKSSQSLL YSTNQKNYLA

WYQQKPGQSP KLLIYWASTR ESGVPDRFSG SGSGTDFTLT ISSVQAEDVA VYYCQQYYSY
      134
RTFGGGTKLE IKRAAPSVFI FPPSDEQLKS GTASVVCLLN NFYPREAKVQ WKVDNALQSG
                                                            236
NSQESVTEQD SKDSTYSLSS TLTLSKADYE KHKVYACEVT HQGLSSPVTK SFNRGE*

Light Chain

DIVMTQSPSSLSVSLGERVTMTCKSSQSLLYSTNQKNYLAWYQQKPGQSPKLLIYWASTRESGVPDRFSGS
GSGTDFTLTISSVQPEDVAVYYCQQYYSYRTFGGGTKLEIKRAVAAPSVFIFPPSEDQVKSGTVSVVCLLNN
FYPREASVKWKVDGVLKTGNSQESVTEQDSKDNTYSLSSTLTLSSTDYQSHNVYACEVTHQGLSSPVTKSF
NRGEC

Heavy Chain

EVQLQQSGAEVVKPGASVKMSCKASGYTFTSYVIHWVRQKPGQGLDWIGYINPYNDGTDYDEKFKGKAT
LTSDTSTSTAYMELSSLRSEDTAVYYCAREKDNYATGAWFAYWGQGVLVTVSSASTKGPSVFPLAPSSRST
SESTAALGCLVKDYFPEPVTVSWNSGSLTSGVHTFPAVLQSSGLYSLSSVVTVPSSSLGTQTYVCNVNHKPS
NTKVDKRVEIKTCGGGSKPPTCPPCPAPEAAGGPSVFLFPPKPKDTLMISRTPEVTCVVVDVSQEDPDVKFN
WYVNGAEVHHAQTKPRETQYNSTYRVVSVLTVTHQDWLNGKEYTCKVSNKALPASIQKTISKDKGQPRE
PQVYTLPPSREELTKNQVSLTCLVKGFYPSDIVVEWESSGQPENTYKTTPPVLDSDGSYFLYSKLTVDKSRW
QQGNVFSCSVLHEALHSHYTQKSLSVSPGK (B)

EVQLVESGGGLVQPGGSLRLSCAASGFTFSRQGMHWVRQAPGKGLEWVAFIKYDGSEK
YHADSVWGRFTISRDNSKNTLYLQMNSLRAEDTAVYYCAREAGGPDYRNGYNYYDFY
DGYYNYHYMDVWGKGTTVTVSS*GILGSGGGSGGGGSGGGGS*QSALTQPPSVSGSPGQ
SVTISCNGTSNDVGGYESVSWYQQHPGKAPKLVIYDVSKRPSGVSDRFSGSKSGNTASL
TISGLQAEDEADYYCKSLTSTRRRVFGTGTKLTVL

FUSION ANTIBODIES FOR HIV THERAPY

CROSS REFERENCE TO RELATED APPLICATION

This application claims the benefit of priority from U.S. Provisional Application No. 61/413,178, filed Nov. 12, 2010, the entire content of which is incorporated by reference.

FIELD OF THE DISCLOSURE

This disclosure generally relates to fusion proteins comprised of an antigen-binding site that binds to an epitope of the CD4 receptor and another antigen-binding site that binds an epitope of HIV. The fusion proteins are useful for treating HIV infection in a subject, decreasing the viral load of HIV in a patient, and/or preventing the transmission of HIV to subjects.

BACKGROUND ART

HIV-1 entry is triggered by interaction of the viral envelope (Env) glycoprotein gp120 with domain 1 (D1) of the T-cell receptor CD4. Binding of CD4 by gp120 induces extensive conformational changes in gp120 leading to formation and exposure of a structure called the co-receptor (coR) binding site, also known as the CD4-induced (CD4i) epitope, in the gp120 protein (Moore et al., *Proc Natl Acad Sci USA* 100(19): 10598-602, 2003). The bridging sheet of gp120 is a critical component of the coR binding site that is highly conserved across genetically diverse HIV-1 isolates from different clades (Huang et al., *Proc Natl Acad Sci USA* 101(9):2706-11, 2004). The coR binding site is typically unformed on free (non-CD4-bound) gp120. It forms after attachment of viruses to target cells through CD4 binding. The bridging sheet is highly immunogenic and elicits a class of antibodies known as CD4-induced (CD4i) antibodies in vivo. However, access of full-size Abs to the CD4i epitope (bridging sheet) is sterically restricted during viral entry into cells, most likely because the large size of an Ab cannot access the tight crypt within gp120 where the bridging sheet resides. Thus, most known full-size CD4i Abs do not have potent antiviral activity. Fragments of CD4i Abs that are smaller in size could potentially gain access to the CD4i epitope during viral entry. For example two Ab fragments, known as Fab and scFv, of known CD4i Abs have been shown to significantly inhibit HIV entry more potently than full-size Abs (Labrijn et al., *J. Virol.* 77: 10557-10565, 2003).

Ibalizumab (iMab) is a potent and broad HIV-1 neutralizing Ab (Jacobson et al., *Antimicrob. Agents Chemother.* 53:450-457, 2009; Kuritzkes et al., *J. Infect. Dis.* 189:286-291, 2004). iMab neutralizes HIV by binding mainly to domain 2 (D2) of the CD4 receptor on host T-cells, thus blocking the ability of HIV to use these CD4 receptors to gain entry into T-cells and produce infection (Burkly et al., *J. Immunol.* 149:1779-178, 1992). In a large panel of primary isolates (more than 100 viruses) tested recently, iMab neutralized 92% of all viruses as defined by 50% inhibition of infection, and 47.4% of viruses as defined by 90% inhibition of infection (FIG. 1). These data, while promising, indicate that there is still a need to further improve the potency and breadth of iMab.

Several antibodies have been reported that target epitopes on HIV Env. m36 polypeptide is a human heavy chain domain Ab fragment that targets the highly conserved, but sterically restricted, CD4i epitope on HIV Env. m36 is a potent and broad cross-reactive HIV-1 inhibitor with CD4i Ab activity in vitro, with a mean IC50 in the hundred nanomolar range (Chen et al., *Proc Natl Acad Sci USA* 105(44):17121-6, 2008). However, similar to other small-size antibody fragments, the m36 polypeptide is predicted to have a short half life in circulation. A long half life is an important indicator for long-lasting antiviral activity. PG9 is another potent and broad anti-HIV-1 antibody, targeting a quaternary epitope of the HIV envelope trimer (Walker et al., *Science* 326, 285-289 (2009)). VRC01 is also a potent and broad anti-HIV-1 antibody, targeting a CD4 binding site epitope on the HIV envelope.

SUMMARY OF THE DISCLOSURE

Disclosed herein are fusion antibodies created to provide both an antigen-binding site that targets the CD4 receptor and an antigen-binding site that targets the HIV envelope. The fusion antibodies disclosed herein provide improved potency and breadth against HIV as compared to monospecific antibodies, and additionally provide high barrier against viral resistance.

In some embodiments, the fusion proteins assume the configuration of an intact IgG molecule directed to a first antigen (which can be any isotype, i.e., $IgG_1$, $IgG_2$, $IgG_3$, and $IgG_4$), connected via a linker at either the C or N terminus of its heavy or light chain to an antigen-binding domain of a second antibody directed to a second antigen.

In specific embodiments, the fusion protein is composed of an anti-CD4 antibody conjugated to an antigen-binding domain of an anti-HIV antibody. Examples of such fusion antibodies include Ibalizumab conjugated to m36, PG9scFv, or VRC01scFv.

In additional embodiments, the anti-CD4 antibody portion of a bispecific fusion protein has been modified and fusion variants with improved affinity for CD4 have been selected by affinity maturation.

In other embodiments, the Fc region of a fusion protein has been engineered to provide a better PK profile, including improved stability (e.g., via introduced LALA mutations) and improved recycling capability.

Pharmaceutical formulations and therapeutic methods utilizing the bispecific fusion proteins disclosed herein are also provided.

BRIEF DESCRIPTION OF THE DRAWINGS

This patent or application file contains drawings executed in color. Copies of this patent or patent application publication with color drawings will be provided by the Office upon request and payment of the necessary fee.

FIG. 6. iMabm36 was shown to have greater potency against iMab-resistant viruses as compared to iMab alone.

Figure 1:
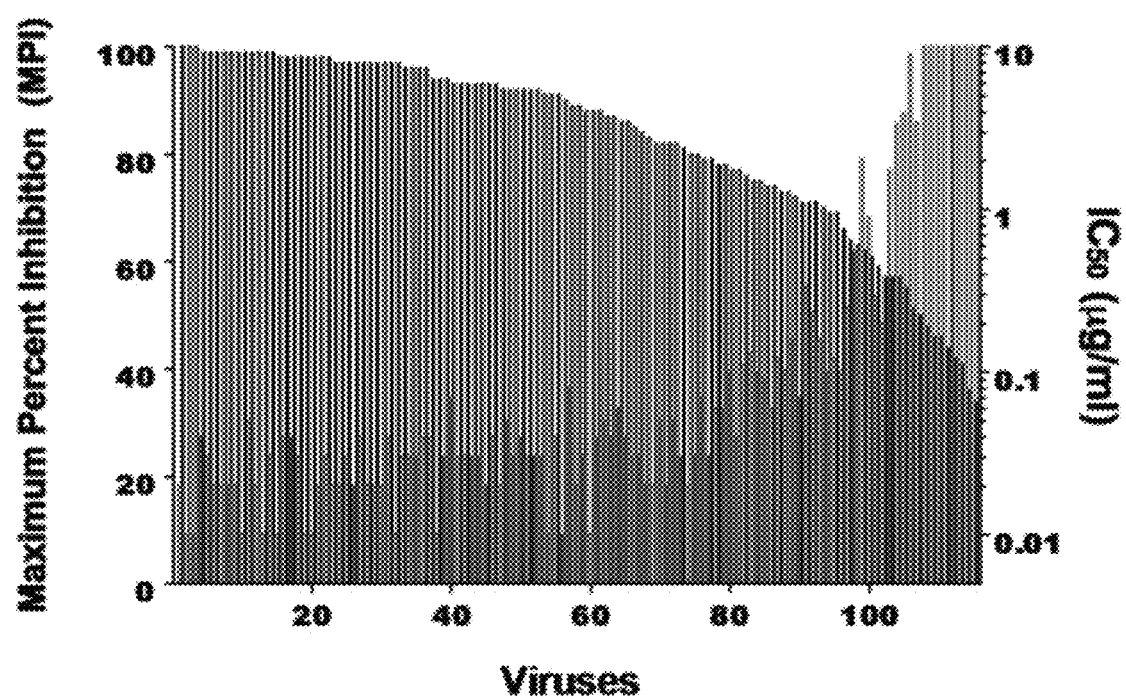
FIG. 1. Ibalizumab neutralization profile on a diverse panel of Env-pseudotyped viruses.

The term "antibody" is used herein broadly and encompasses intact antibody molecules, which include intact polyclonal, monoclonal, monospecific, polyspecific, chimeric, humanized, human, primatized, single-chain, single-domain, synthetic and recombinant antibodies, and antibody fragments that have a desired activity or function.

The term "chimeric antibody" refers to antibodies containing polypeptides from different sources, e.g., different species or different antibody class or subclass. Examples of chimeric antibodies include an antigen-binding portion of a murine monoclonal antibody fused an Fc fragment of a human immunoglobulin. Methods for making chimeric antibodies are known in the art; for example, methods described in patents by U.S. Pat. No. 4,816,397 to Boss et al. and U.S. Pat. No. 4,816,567 to Cabilly et al.

The term "humanized antibody" refers to antibodies that contain non-human sequence elements in a human immunoglobulin backbone or framework. Generally, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having a desired specificity, affinity and capacity. In some instances, framework region (FR) residues of the human immunoglobulin are also replaced by non-human residues. Humanized antibodies may also, in some instances, contain residues that are not found in either the recipient antibody or the donor antibody and introduced to further refine antibody performance. In general, a humanized antibody contains substantially all of at least one, and typically two, variable domains, in which all or substantially all of the hypervariable regions correspond to those of a non-human immunoglobulin and all or substantially all of the framework regions are those of a human immunoglobulin sequence. A humanized antibody optionally also contains at least a portion of an immunoglobulin constant region (Fc), typically that of a human immunoglobulin. Methods for making humanized antibodies are documented in the art; see, for example, by U.S. Pat. No. 5,225,539 to Winter and U.S. Pat. No. 4,816,397 to Boss et al.

The term "primatized antibody" refers to antibodies that contain non-primate sequence elements in a primate immunoglobulin backbone or framework. For example, primatized antibodies can be made from a primate immunoglobulin (recipient antibody) by replacing residues in a hypervariable region (CDRs) of the recipient antibody with residues from a hypervariable region of a donor antibody from a non-primate species such as mouse, rat, rabbit or nonhuman primate having a desired specificity, affinity and capacity. Alternatively, primatized antibodies can be made suitable for administration to a desirable primate species by using a recipient immunoglobulin having non-primate sequences or sequences from a different primate species and introducing the Fc fragment, and/or residues, including particularly framework region residues, from the desirable primate, into the recipient immunoglobulin. Examples of primatized antibodies include "monkeynized" antibodies disclosed herein in the Examples section.

The term "monospecific antibody" refers to antibodies that recognize and bind to one epitope.

The term "polyspecific antibody" refers to antibodies formed from at least two separate antibodies and binding to multiple (i.e., two or more) separate epitopes.

As described above, the term "antibody" also includes fragments of an intact antibody, or "antibody fragments", including particularly antigen-binding fragments of an intact antibody. Examples of antigen-binding fragments include, but are not limited to, Fab fragments (consisting of the VL, VH, CL and CH1 domains), Fab' fragments (which differs from Fab fragments by having an additional few residues at the C-terminus of the CH1 domain including one or more cysteines from the antibody hinge region), (Fab')$_2$ fragments (formed by two Fab' fragments linked by a disulphide bridge at the hinge region), Fd fragments (consisting of the VH and CH1 domains), Fv fragments (referring to a dimer of one heavy and one light chain variable domain in tight, non-covalent association which contains a complete antigen recognition and binding site), dAb fragments (consisting of a VH domain), single domain fragments (VH domain, VL domain, VHH domain, or VNAR domain), isolated CDR regions, scFv (or "single chain Fv", referring to a fusion of the VL and VH domains, linked together via a linker), and other antibody fragments that retain antigen-binding function.

The term "CDR" or "complementarity determining region" refers to the hypervariable regions within the variable domain of an antibody. There are 3 CDRs in each of the heavy chain and light chain variable domains, and are composed of amino acid residues responsible for antigen-binding. The term "framework region" or "FR" refers to the more conserved portions of the variable domains and is composed of residues other than the hypervariable region residues.

The term "antigen-binding site" of an antibody means a conformation and/or configuration formed by amino acids of the antibody to which an antigen binds. For example, the three CDRs of each of the VH and VL domains interact to define an antigen-binding site on the surface of the VH-VL dimer. Together, the six CDRs confer antigen-binding specificity to the antibody. It should be noted, however, a single variable domain (i.e., VH or VL) can also recognize and bind antigen, albeit often less effectively than the whole binding site with all six CDRs.

The term "neutralizing antibody" refers to an antibody that inhibits, reduces or completely prevents HIV-1 infection. Whether an antibody is a neutralizing antibody can be determined by in vitro assays described in the Examples section hereinbelow.

The term "potent neutralizing antibody" refers to an antibody which, when used at a low concentration, reduces HIV-1 infection by at least 50%, 60%, 70%, 80%, 90%, 95%, 99% or greater. Concentrations below 50 µg/ml, between 1 and 50 µg/ml, or even below 1 µg/ml, are considered "low concentrations". In some embodiments, low concentrations are concentrations in the picomolar range, such as 10-900 ng/ml, and include any concentration in that range, such as 800, 700, 600, 500, 400, 300, 200, 100, 75, 50, 25, 10 ng/ml, or even less than 10 ng/ml.

The term "broad neutralizing antibody" refers to an antibody which inhibits HIV-1 infection, as defined by a 50% inhibition of infection in vitro, in more than 50%, 60%, 70%, 80%, 90%, 95%, 99% or greater, of a large panel of (greater than 100) HIV-1 envelope pseudotyped viruses and viral isolates.

The term "fragment" as used herein refers to a physically contiguous portion of the primary structure of a biomolecule. In the case of proteins, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. For example, the m36 fragment is 117 amino acids long. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "fusion protein" refers to two or more peptides of different origins connected to each other via a linker or linkers. For example, a fusion protein can include a protein conjugated to an antibody. Other examples include, an antibody conjugated to a different antibody or an antibody conjugated to a Fab fragment. The Fab fragment can be conjugated to the N terminus or C terminus of the heavy or light chain of the antibody, or other regions within the antibody. The term fusion protein and fusion construct are used herein interchangeably.

A "peptide" is any compound formed by the linkage of two or more amino acids by amide (peptide) bonds, usually a polymer of alpha-amino acids in which the alpha-amino group of each amino acid residue (except the NH2 terminus) is linked to the alpha-carboxyl group of the next residue in a linear chain. The terms peptide, polypeptide and poly(amino acid) are used synonymously herein to refer to this class of compounds without restriction as to size, unless indicated to the contrary. Members of this class having a large size are also referred to as proteins and include antibodies.

The term "linker" refers to a chemical moiety that connects one peptide to another, e.g., one antibody to another. Linkers can also be used to attach antibodies to labels or solid substrates. A linker can include amino acids. Linkers can be straight or branched, saturated or unsaturated carbon chains. They can also include one or more heteroatoms within the chain or at the termini of the chains. By "heteroatoms" is meant atoms other than carbon which are chosen from the group comprising of oxygen, nitrogen, sulfur, phosphorus, boron and halogen. In specific embodiments, linkers are peptides. The use of a linker may or may not be advantageous or needed, depending on the specific antibody pairs. Methods and techniques for the attachment of a linker to an antibody are known in the art. For a treatise on this subject, the reader is referred to *Bioconjugate Techniques*, G. Hermanson, Academic Press, 1996.

Fusion Antibody Targeting Both CD4 and HIV

This disclosure is directed to fusion antibodies that contain an antigen-binding site that targets the CD4 receptor and another antigen-binding site that targets the HIV envelope. Fusion antibodies having specificities towards simply two different antigens are also referred to herein as bispecific antibodies. Bispecific fusion antibodies can be modified to include additional antigen binding sites to provide other polyspecific antibodies.

Generally speaking, the structure of the fusion proteins disclosed herein is composed of an intact IgG molecule directed to a first antigen, connected via a linker at either the C or N terminus of its heavy chain or light chain to an antigen-binding fragment of a second antibody directed to a second antigen. For example, a fusion antibody having dual specificities towards the CD4 receptor and HIV can be formed by conjugating an intact anti-CD4 antibody with an antigen-binding fragment of anti-HIV antibody. Conversely, a fusion antibody having dual specificities towards the CD4 receptor and HIV can be formed by conjugating an intact anti-HIV antibody with an antigen-binding fragment of anti-CD4 antibody. In either scenario, a bispecific fusion antibody contains an antigen-binding site that binds to an epitope on the CD4 receptor and another antigen-binding site that binds to an epitope on the HIV envelope.

Anti-CD4 antibodies have been described in the art and can also be readily generated as the protein sequence of the CD4 receptor is available to those skilled in the art. As a member of the immunoglobulin superfamily, CD4 has four immunoglobulin domains (D1 to D4) that are located on the extracellular surface of the cell. CD4 uses its D1 domain to interact with the $\beta_2$-domain of MHC class II molecules.

In some embodiments, antibodies directed principally to the second immunoglobulin-like domain (D2) (amino acid positions 98-180) of the CD4 receptor are used in forming the bispecific fusion antibodies herein. Antibodies directed to the D2 domain of CD4 have the desirable property of blocking HIV infection without interfering with immune functions mediated by interaction of CD4 with the major histocompatibility complex (MHC) class II molecules. In specific embodiments, the anti-CD4 antibody used in forming a bispecific fusion binds to an epitope located in the BC-loop of D2 near the D1-D2 junction of the CD4 receptor (amino acids 121-127). In other embodiments, the anti-CD4 antibody binds to the FG-loop of D2 (amino acids 163-165) and part of D1 (amino acids 77-96). The anti-CD4 antibody used in forming a fusion protein can bind to one or more or all of these regions, i.e., D1, D1-D2 junction, D2, the BC or FG loop of D2, or any combination thereof. The above amino acid numbering corresponds to positions of the mature form of the receptor, not including the signal peptide. The amino acid sequence of the human CD4 receptor is available in GenBank under Accession No. AAA16069.1 and is also set forth in SEQ ID NO: 34, in which amino acids 1-25 represent a signal peptide, amino acids 26-122 constitute D1, and amino acids 123-205 constitute D2.

A specific example of an anti-CD4 antibody suitable for use in forming a bispecific fusion antibody is Ibalizumab (previously known as TNX-355, or hu5A8), which is a humanized, anti-CD4 monoclonal antibody. Ibalizumab potently blocks infection by a broad spectrum of HIV-1 isolates and targets an epitope located in the BC-loop of D2 near the D1-D2 junction of the CD4 receptor, without interfering with immune functions mediated by interaction of CD4 with the major histocompatibility complex (MHC) class II molecules.

Anti-HIV Env antibodies have also been described in the art and can also be readily generated by those skilled in the art. The env gene encodes a precursor protein, gp160. During HIV reproduction, the endogenous enzymes of the host cell cleave gp160 into gp120 and gp41. Three gp120 molecules form a trimer which is anchored to the viral membrane, or envelope, via non-covalent interactions with the transmembrane protein, gp41. Binding of CD4 by gp120 induces extensive conformational changes in gp120 leading to formation and exposure of a structure called the co-receptor (coR) binding site, also known as the CD4-induced (CD4i) epitope, in the gp120 protein (Moore et al., *Proc Natl Acad Sci USA* 100(19): 10598-602, 2003). The bridging sheet of gp120 is a critical component of the coR binding site that is highly conserved across genetically diverse HIV-1 isolates from different clades (Huang et al., *Proc Natl Acad Sci USA* 101(9):

2706-11, 2004). The coR binding site is typically unformed on free (non-CD4-bound) gp120. It forms after attachment of viruses to target cells through CD4 binding. The bridging sheet is highly immunogenic and elicits a class of antibodies known as CD4-induced (CD4i) antibodies in vivo. However, access of full-size Abs to the CD4i epitope (bridging sheet) is sterically restricted during viral entry into cells, most likely because the large size of an Ab often cannot access the tight crypt within gp120 where the bridging sheet resides. Fragments of CD4i Abs that are smaller in size could potentially gain access to the CD4i epitope during viral entry. For example, two Ab fragments, known as Fab and scFv, of known CD4i Abs have been shown to significantly inhibit HIV entry more potently than full-size Abs (Labrijn et al., *J. Virol.* 77: 10557-10565, 2003), and such antibody fragments are suitable for use in forming a bispecific fusion antibody in accordance with this disclosure.

In specific embodiments, anti-HIV antibodies used herein in forming a bispecific fusion antibody are directed to an epitope on an envelope protein of HIV, e.g., gp120 monomer or trimer, or gp41. In more specific embodiments, the anti-HIV antibodies used in forming a bispecific fusion may bind to the CD4 binding site on the HIV envelope at amino acids 279-460, the V1/V2 and V3 regions of the HIV envelope trimer at amino acids 125-196 and 296-331, and/or the CD4 bridging sheet site on the HIV envelope at amino acids 332-444. Examples of anti-HIV antibodies suitable for use herein include, but are not limited to, m36, PG9, and VRC01. The amino acid sequence of HIV gp160 is available in GenBank under Accession No. AAB60578.1, and is also set forth in SEQ ID NO: 35, in which amino acids 1-30 represent a signal peptide, and amino acids 31-509 represent the mature gp120.

In certain embodiments, a fusion antibody having dual specificities towards the CD4 receptor and HIV is composed of an intact anti-CD4 antibody, conjugated with (i.e., covalently linked to) an antigen-binding fragment of anti-HIV antibody. As defined above, an antigen-binding fragment of anti-HIV antibody including Fab fragments, Fab' fragments, (Fab')$_2$ fragments, Fd fragments, Fv fragments, dAb fragments, single domain fragments, isolated CDR regions, scFvs, and other antibody fragments that retain HIV-binding function of an anti-HIV antibody.

In a specific embodiment, a single domain antibody fragment of an anti-HIV antibody, e.g., m36, is fused to an intact anti-CD4 antibody. In some embodiments, the single domain antibody fragment is fused to the C-terminus of the heavy chain or light chain of the anti-CD4 antibody. In other embodiments, the single domain antibody fragment is fused to the N-terminus of the heavy or light chain of the anti-CD4 antibody.

In another specific embodiment, a single chain Fv fragment (i.e., scFv) of an anti-HIV antibody is fused to an intact anti-CD4 antibody. Similarly, the scFv fragment can be fused to the C-terminus or N-terminus of either the heavy chain or light chain of the anti-CD4 antibody. In some embodiments, the scFv fragment is a single chain of the VH domain linked to the N-terminus of the VL domain of a relevant anti-HIV antibody; while in other embodiments, the scFv fragment is a single chain of the VH domain linked to the C-terminus of the VL domain of a relevant anti-HIV antibody.

The linkage between the two antibody components, i.e., between the anti-CD4 antibody portion and the anti-HIV antibody portion, and also between the VH and VL domains of an scFv fragment, is achieved by a peptide linker. The length of a linker is generally in the range of 5 to 50 amino acids, and in specific embodiments, in the range of 9-25 amino acids, such as 9, 12, 16, 20 or 24 amino acids. The linkers can be synthetic or native human antibody-derived sequences, or a combination of both. Generally speaking, the linkers are principally composed of relatively small, neutral amino acids, such as Glycine, Serine, Alanine, and can include multiple copies of a sequence enriched in Glycine and Serine, such as multiple copies of GGGGS (SEQ ID NO: 33). Examples of linkers suitable for use herein include those set forth in SEQ ID NO: 3, 12, 14, 23 and 32.

The bispecific fusion antibodies disclosed herein can be produced by utilizing techniques available to those skilled in the art. For example, DNA molecules encoding a desirable bispecific fusion antibody can be constructed based on the coding sequence of the two antibody components of the fusion using molecular cloning techniques. The resulting DNAs can be placed into expression vectors which are then transfected into host cells such as *E. coli* cells, simian COS cells, Chinese Hamster Ovary (CHO) cells, human embryonic kidney 293 cells, or myeloma cells including murine myeloma cells that do not otherwise produce immunoglobulin protein, to obtain the synthesis of monoclonal antibodies in the recombinant host cells. For example, an expression vector encoding a heavy chain of an anti-CD4 antibody fused to an anti-HIV antibody fragment, and an expression vector encoding the light chain of the anti-CD4 antibody, can be co-transfected into a host cell for expression. Antibody-containing culture supernatants can be collected for purification of antibodies.

The produced fusion antibodies can be evaluated in in vitro assays to assess their functionality, e.g., binding to the CD4 receptor, binding to the HIV envelope, anti-HIV potency and breadth. In specific embodiments, this disclosure provides potent and broad bispecific fusion antibodies, with potency and breadth being defined as hereinabove. These antibodies are described in more details in the Examples section.

Modifications to Antibodies

Humanization and Primatization

In cases where the fusion antibody or the two antibodies forming the bispecific fusion antibody are non-human antibodies, the antibody can be "humanized" to reduce immunogenicity to a human recipient. Methods for humanizing non-human antibodies have been described in the art. See, e.g., Jones et al., *Nature* 321:522-525 (1986); Riechmann et al, *Nature* 332:323-327 (1988); Verhoeyen et al., *Science* 239: 1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. It is important to humanize a non-human antibody while retaining high affinity for the antigen. To this end, three dimensional immunoglobulin models are commonly available and suitable for use in analyzing proposed humanized sequences in comparison to the parental non-human antibodies. Such analysis permits identification of residues likely involved in recognition and binding of the antigen, and therefore rational design of humanized sequences that retain the specificity and affinity for the antigen.

In specific embodiments, bispecific fusion antibodies are formed from an anti-CD4 antibody which has been humanized and an anti-HIV human or humanized antibody. For example, ibalizumab is an example of a humanized anti-CD4 antibody, and m36 is an example of the variable domain of a human anti-HIV antibody.

Similarly, a fusion antibody or the two antibodies forming the fusion can be "primatized" to reduce immunogenicity to another primate, non-human recipient, e.g., a rhesus recipient. Residues from the variable domain of a donor antibody (such as a non-primate antibody or an antibody of a primate species different from the recipient primate) are "imported" into a nonhuman primate recipient immunoglobulin molecule, resulting in antibodies in which some hypervariable region residues and possibly some FR residues of a nonhuman primate antibody are substituted by residues from analogous sites of donor antibodies. Alternatively, primatized antibodies can be made for use in a desirable primate species by using a recipient immunoglobulin having non-primate sequences or sequences from a different primate species by introducing the Fc fragment, and/or residues, including particularly framework region residues, from the desirable primate, into the recipient immunoglobulin. A "monkeynized" version of Ibalizumab, and a monkeynized version of anti-HIV antibody PG9 scFv, are disclosed in the Examples hereinbelow.

Affinity Maturation

One or more hypervariable region residues of an antibody can be substituted to select for variants that have improved biological properties relative to the parent antibody by employing, e.g., affinity maturation using phage or yeast display. For example, the Fab region of an anti-CD4 antibody or an anti-HIV antibody can be mutated at several sites selected based on available structural information to generate all possible amino substitutions at each site. The antibody variants thus generated are displayed in a monovalent fashion from phage particles or on the surface of yeast cells. The displayed variants are then screened for their biological activity (e.g. binding affinity). Examples of ibalizumab variants having high affinities are described herein below. These ibalizumab variants can be used in forming bispecific fusion antibodies.

Modifications to the Fc Region

The fusion antibody or the intact antibody used in forming the fusion, which can be of any IgG isotype from any primate species including human, can be modified to improve certain biological properties of the antibody, e.g., to improve stability, to enhance or reduce effector functions such as antigen-dependent cell-mediated cyotoxicity (ADCC) and/or complement dependent cytotoxicity (CDC) of the antibody, improved or decreased internalization and/or recycling, among others.

For example, the Fc fragment of ibalizumab (derived from human Ig4) can be replaced with human IgG1 carrying the so-called LALA mutations that reduce effector function mediated through FcRs (except FcRn). Such modification has been shown herein to improve the stability of the resulting antibody by about 5 fold. The LALA mutation can also be introduced into an IgG4 background. In another example, the IgG1 Fc fragment can be modified with the pair of mutations, M428L/N434S, to improve the recycling of the antibody via the antibody salvage pathway. This pair of mutations, introduced in the IgG1-LALA version of ibalizumab, has led to an additional about 3 fold improvement in PK of the resulting antibody.

Still another type of modification involves alteration of the glycosylation pattern of a parent antibody, including deletions of one or more carbohydrate moieties found in the parent antibody, or addition of one or more carbohydrates (via addition of one or more glycosylation sites) that are not present in the parent antibody Pharmaceutical Formulations Pharmaceutical formulations of the fusion antibody proteins disclosed can be prepared by mixing a fusion protein with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The formulation can contain more than one active compound, e.g., one or more fusion antibodies, in combination with one or more additional beneficial compound for preventing and treating HIV infections.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

Methods of Treatment and Prevention

In a further aspect, the bispecific fusion antibodies disclosed herein, optionally provided in pharmaceutically acceptable carrier, are employed for the treatment and prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention" of HIV infection means the onset of HIV infection is delayed, and/or the incidence or likelihood of HIV infection is reduced or eliminated.

The term "prevention" of HIV transmission means the incidence or likelihood of HIV being transmitted from one individual to another (e.g., from an HIV-positive woman to the child during pregnancy, labor or delivery, or breastfeeding) is reduced or eliminated.

The term "subject" refers to any primate subject, including human and rhesus subjects.

To treat and/or prevent HIV infection, a therapeutic amount of a fusion antibody disclosed herein is administered to a subject in need.

The term "therapeutically effective amount" means the dose required to effect an inhibition of HIV infection so as to treat and/or prevent HIV infection. The dosage of a fusion antibody depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of a fusion antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of the fusion antibodies provided in a controlled release matrix can be employed.

The fusion antibodies can be administered to the subject by standard routes, including the oral, transdermal, parenteral (e.g., intravenous, intraperitoneal, intradermal, subcutaneous or intramuscular). In addition, the antibodies can be introduced into the body, by injection or by surgical implantation or attachment such that a significant amount of a desirable antibody is able to enter blood stream in a controlled release fashion.

The description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The present description is further illustrated by the following examples, which should not be construed as limiting in any way. The contents of all cited references (including literature references, issued patents, and published patent applications as cited throughout this application) are hereby expressly incorporated by reference.

EXAMPLE-1

Construction and Testing of iMabm36

This Example describes the construction and testing of a novel bispecific HIV-1 neutralizing antibody (Ab) for the prevention and treatment of HIV/AIDS which was named iMabm36. iMabm36 is composed of the anti-CD4 Ab ibalizumab (iMab) linked to two copies of the anti-CD4-induced Ab m36. iMabm36 is shown herein to have significantly increased antiviral potency and breadth over iMab and m36 alone. In particular, it can potently inhibit viral entry of all iMab-resistant viruses tested. Mechanistically, it is shown therein that iMabm36 activity requires CD4 binding and is m36 sensitivity dependent. The inter-dependency of this dual mechanism of action enables the high potency and breadth of iMabm36. As almost all HIV-1 isolates use CD4 as a primary entry receptor and the m36 targeting site is highly conserved across all HIV-1 isolates, targeting these two sites is believed to provide a high barrier against viral resistance. iMabm36 has been shown to be stable in vitro, and is believed to have improved pharmacokinetics as compared to m36 alone and is unlikely to be immunogenic.

Figure 2:
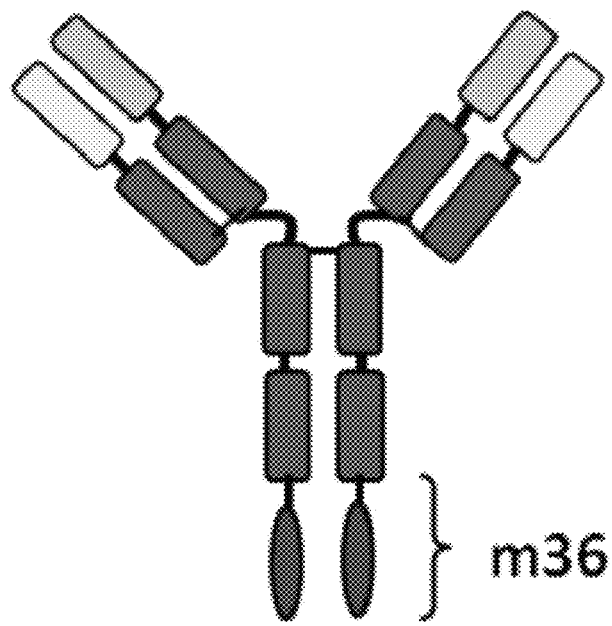
FIG. 2. Schematic representation of the iMab-m36 fusion construct. Orange, Yellow, and Blue represent the Variable Heavy, Variable Light, and Constant chains of ibalizumab, respectively. Red represents the m36 polypeptide.

Construction and expression of iMabm36 fusion Ab. A bi-specific fusion Ab was constructed based on a derivative IgG1 version of iMab called MV1 and m36. As shown in the schematic in FIG. 2 and the sequence in FIG. 11, m36 was linked to the C-terminus of the heavy chain of MV1 via a flexible (G4S)x3 linker peptide (GGGGSGGGGSGGGGSG, SEQ ID NO: 3). In brief, cDNA sequence of the fusion construct was generated by overlap PCR and subsequently cloned into the pVAX expression plasmid through unique restriction sites.

Figure 3:
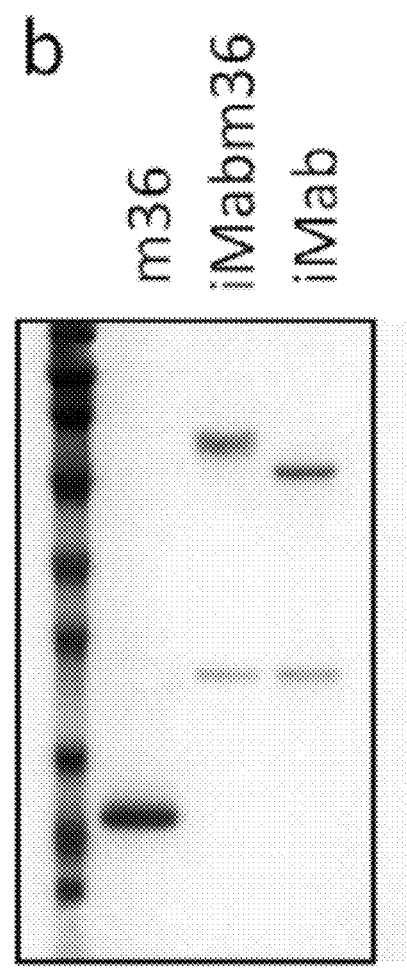
FIG. 3. SDS-PAGE showing expression of purified m36, iMab36 fusion, and iMab. Left-most lane contains a size marker.
Figure 4:
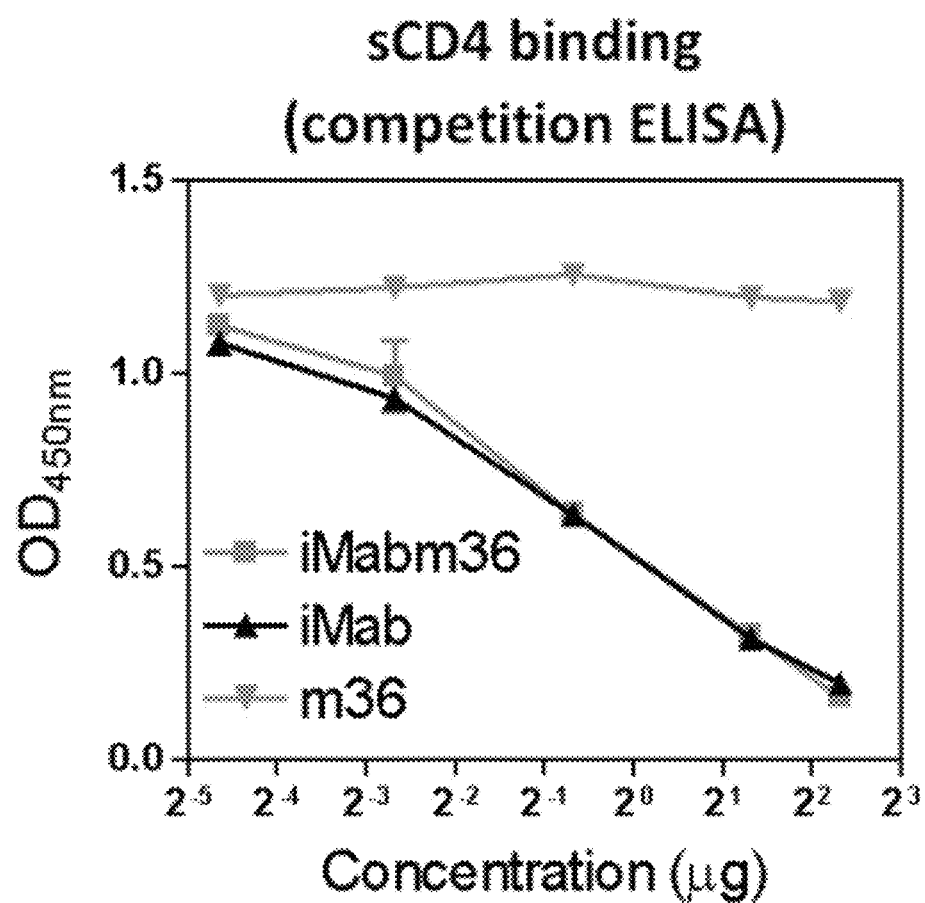
FIG. 4. iMabm36 binds sCD4. X-axis indicates increasing levels of the unlabeled constructs for iMab36 (pink), iMab (black), or m36 (green). Y-axis indicates the competitive level of binding of HRP-labeled ibalizumab to sCD4.
Figure 5:
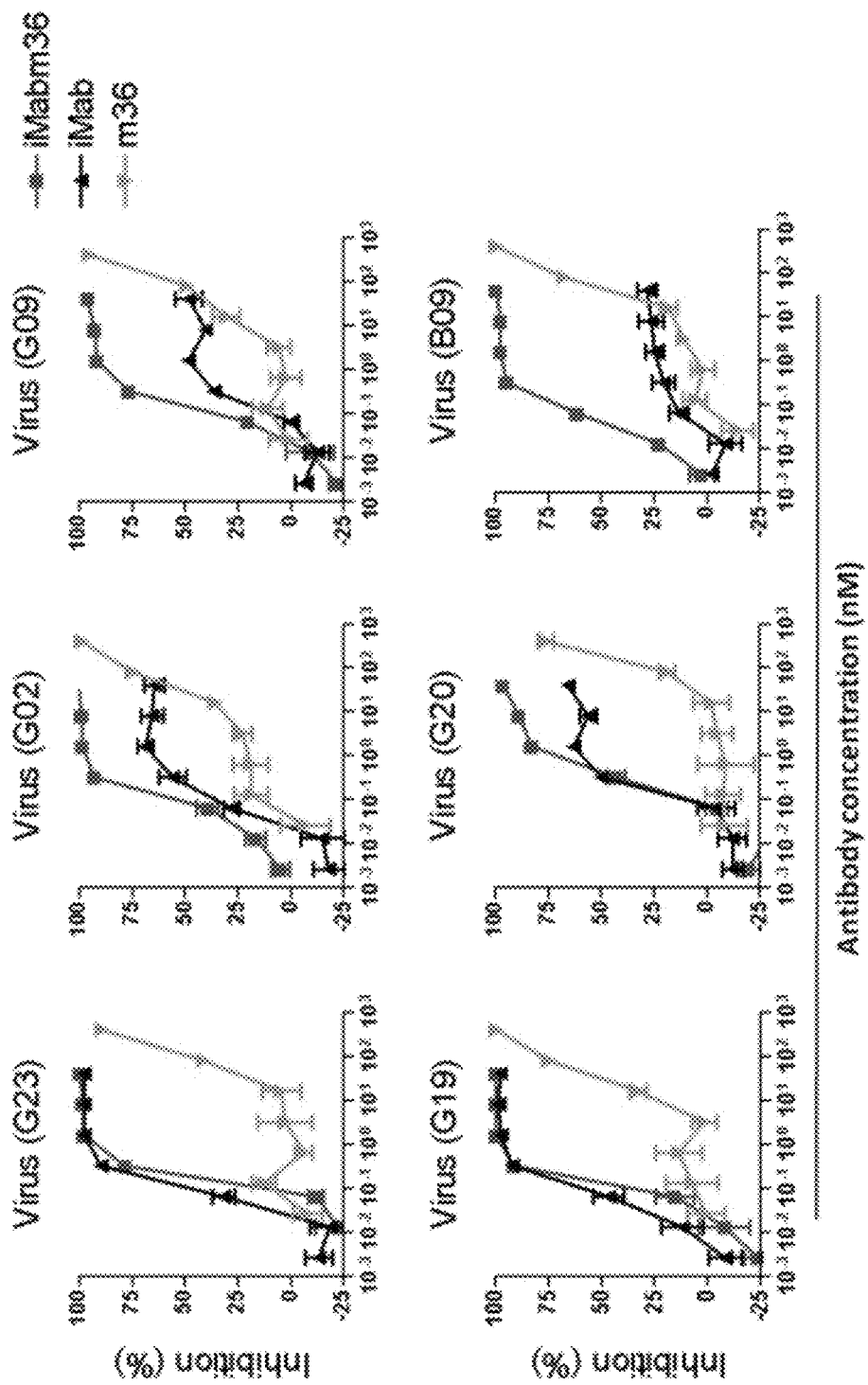
FIG. 5. iMab36 was shown to be active against ibalizumab-sensitive and -resistant viruses. iMab-sensitive (left column) or iMab-resistant (right two columns) viruses were tested for their viral activity in the presence of the neutralizing constructs iMabm36 (pink), iMab (black), or m36 (green).

The iMabm36 fusion Ab was expressed by transient co-transfection of pVAX vectors expressing 1) heavy chain iMabm36 fusion and 2) light chain ibalizumab into human embryonic kidney 293 cells. Ab-containing culture supernatants were filtered and purified by affinity chromatography using a Protein A Sepharose column (FIG. 3). The average yield was 1-5 μg/ml of culture medium.

iMabm36 retains CD4 binding activity in vitro. Purified iMabm36 was assessed for soluble CD4 (sCD4) binding in a competition ELISA assay. In brief, a 96-well plate was coated with sCD4. A fixed concentration of HRP labeled iMab was then mixed with increasing concentrations of iMabm36 or unlabeled iMab and measured for sCD4 binding competition. As shown in FIG. 4, iMabm36 competed with iMab-HRP labeled Ab for CD4 binding with equal potency as compared to the parental unlabeled iMab, indicating the functional CD4 binding properties of the iMabm36 fusion protein. As expected, m36 alone did not bind to sCD4.

iMabm36 fusion Ab improves antiviral potency and breadth as compared to iMab or m36 alone. To test whether the fusion of m36 to the C-terminal of iMab could result in more potent antiviral activity, iMabm36, iMab and m36 were each examined in a TZM-b1 based HIV-1 Env pseudotyped neutralization assay against a panel of 6 viruses that included iMab sensitive and resistant viruses. As shown in FIG. 5, iMabm36 demonstrated a similar potency against iMab sensitive viruses (G19 and G23) as compared to iMab alone. While iMab can only achieve a maximal percent of inhibition (MPI) of 25% to 75% for iMab resistant viruses (G02, G09, G20, and B09), the iMabm36 fusion could neutralize all four of these viruses and achieved 100% MPI at low nanomolar concentrations. Consistent with previous publication, the 50% inhibitory activity of m36 is within the range of hundreds of nanomolar concentrations.

In a separate experiment, iMabm36 activity was further examined against all iMab-resistant viruses in the inventors' collection (FIG. 6). Among 13 iMab-resistant viruses tested (defined as a MPI of less than 100%), all could be neutralized by iMabm36 with 100% MPI, except for the virus G12 which was neutralized by up to 90% MPI. The mean concentration required to achieve 100% viral neutralization by iMabm36 is around 0.5 μg/ml (2.8 nM). Also, iMabm36 was active in a PMBC based neutralization assay (data not shown).

Figure 7:
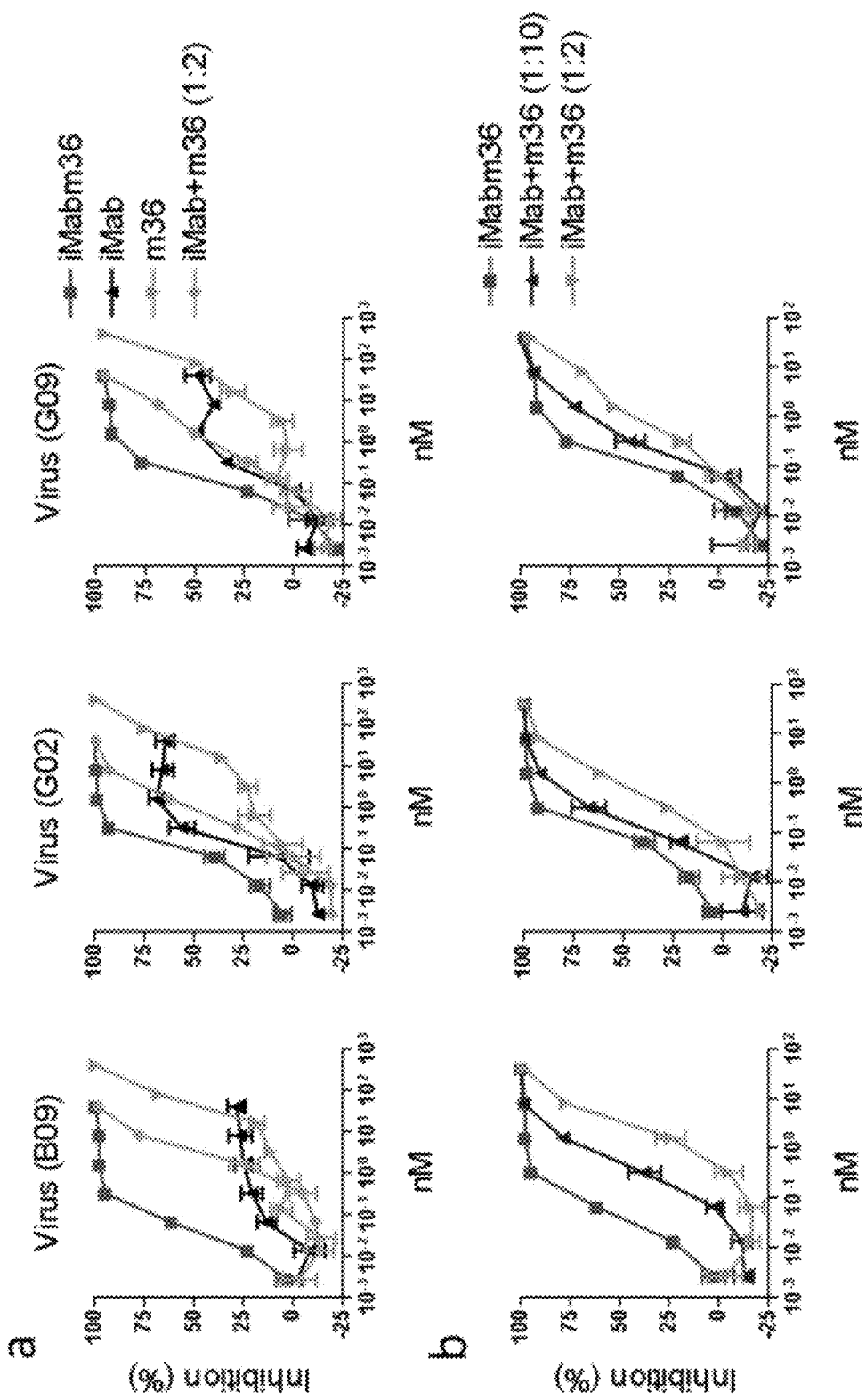
FIG. 7. Cell surface anchoring of m36 by fusing it to iMab was shown to improve its antiviral potency.

Increased antiviral potency of iMabm36 compared to iMab and m36 mixture. The results of FIG. 5 indicated that iMabm36 was more active than its individual components iMab and m36. To investigate if the high antiviral activity of iMabm36 could also be achieved by simply mixing iMab and m36, a neutralizing assay was performed using iMab and m36 at a molar ratio of 1:2 because one iMab carries two m36 peptides in the iMabm36 fusion. As shown in FIG. 7a, mixing iMab and m36 improved not only the antiviral activity of the respective components, but also achieved 100% neutralization of the iMab-resistant viruses tested. These results indicate that iMab and m36 contribute to the antiviral activity in an additive or synergistic manner. In comparison with the mixing of iMab and m36 components, the iMabm36 fusion Ab demonstrated even greater antiviral activity with at least 10-fold enhancement at the same molar concentrations tested.

To test the hypothesis that iMabm36 acts through increasing m36 local concentration, iMab was mixed with an excess of m36 at a molar ratio of 1:10. As shown in FIG. 7b, mixing iMab and m36 at a 1:10 ratio was more potent than that of the 1:2 ratio in FIG. 7a. Notably, even with a five times excess of m36, the mixture using individual components was still less potent than m36 fused to iMab.

Figure 8:
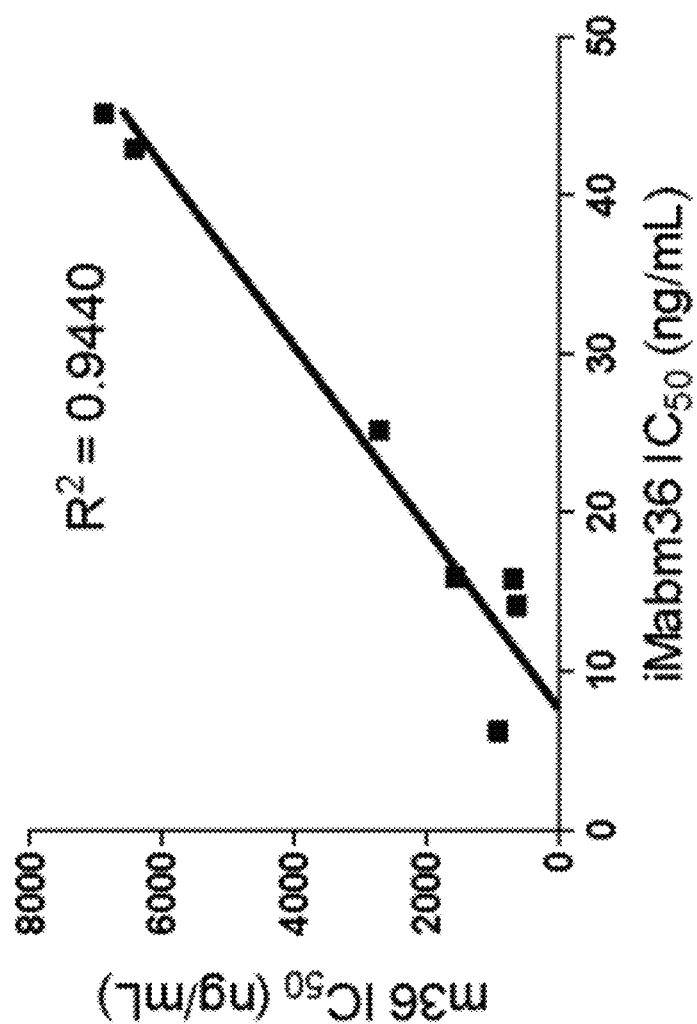
FIG. 8. Sensit ies. An epitope can be a conformational epitope or a linear epitope. A conformational epitope is formed by discontinuous sections of an antigenic molecule, or formed by multiple molecules. In the case where the antigen is a protein, a conformational epitope can be formed by discontinuous amino acid residues of the same protein molecule, or by amino acid residues on different molecules of the protein (e.g., a quaternary epitope formed by a multimer of the protein). A linear epitope is formed by continuous sections of an antigen, e.g., a continuous sequence of amino acids of a protein antigen.

Improved potency of the iMabm36 fusion against iMab-resistant viruses is conferred by viral sensitivity to m36. To better understand the contribution of m36 in the context of the iMab36 fusion, the inventors analyzed the correlation of ibalizumab-resistant virus sensitivity to m36 versus iMabm36. As shown in FIG. 8, a strong correlation was observed between the IC50 of m36 and the IC50 of iMabm36. This result supports the notion that, in the context of iMab-resistant viruses, the sensitivity of iMabm36 is determined by the virus sensitivity to m36.

Figure 9:
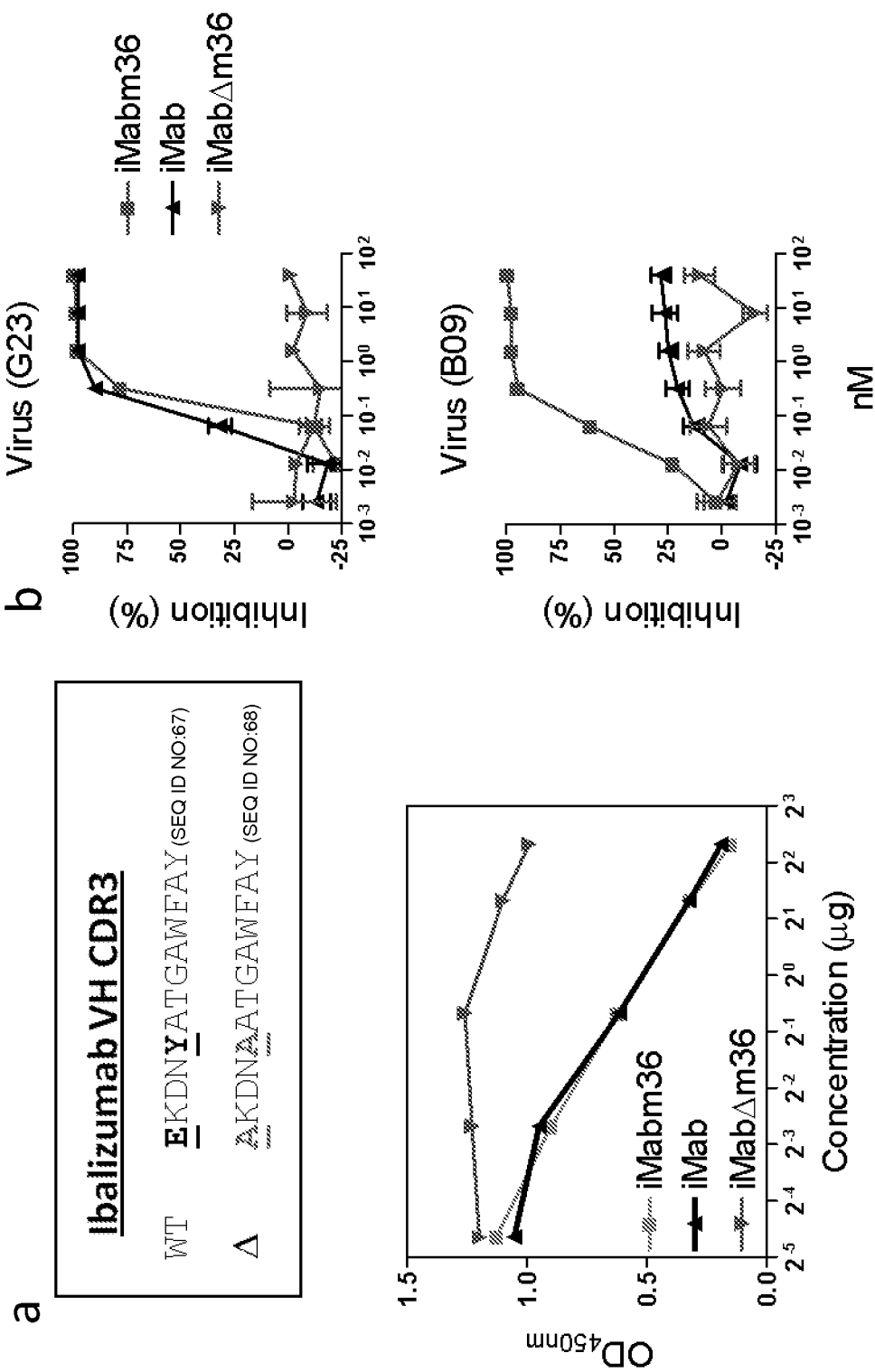

Antiviral potency of iMabm36 is dependent on its CD4 binding. To understand the mechanism of antiviral activity of the iMab36 fusion, two contact amino acid residues in the iMab heavy chain variable CDR3 region were substituted with alanine residues. The CDR3 regions of the wt and mutant heavy chains of iMab are set forth in FIG. 9a and SEQ ID NOS: 35 and 36 respectively. The mutant fusion Ab (iMabΔm36) was purified and tested for its CD4 binding ability in vitro. As shown in FIG. 9a, iMabΔm36 could no longer compete with iMab-HRP for sCD4 binding, suggesting that these two mutations abolished the CD4 binding activity of iMabm36. In a virus neutralization assay, iMabΔm36 lost its virus neutralization activity (FIG. 9b). This result suggests that the antiviral activity of iMabm36 is dependent on its CD4 binding. In other words, anchoring of m36 via iMab binding to CD4 is critical for iMabm36 antiviral activity.

In vitro stability of iMabm36. To assess the stability of iMabm36, the inventors first generated high titers of rabbit anti-m36 immune serum. To do so, rabbits were immunized with purified m36 protein (300 μg/dose) in CFA at week 0 and subsequently boosted in IFA twice at weeks 4 and 8. Anti-m36 Ab titers were determined in the serum sample collected 4 weeks post last boost immunization. The in vitro stability of the iMabm36 fusion Ab was determined by incubation of the fusion Ab in 20% serum in PBS at 37° C. for up to 7 days. Aliquots of the untreated (day 0) and treated fusion Ab were taken at the indicated time points and stored at −20° C. The presence of intact iMabm36 was examined by the functional binding activity of iMabm36 to sCD4 and determined by anti-iMab Fc direct ELISA and anti-m36 sandwich ELISA, respectively.

Figure 10:
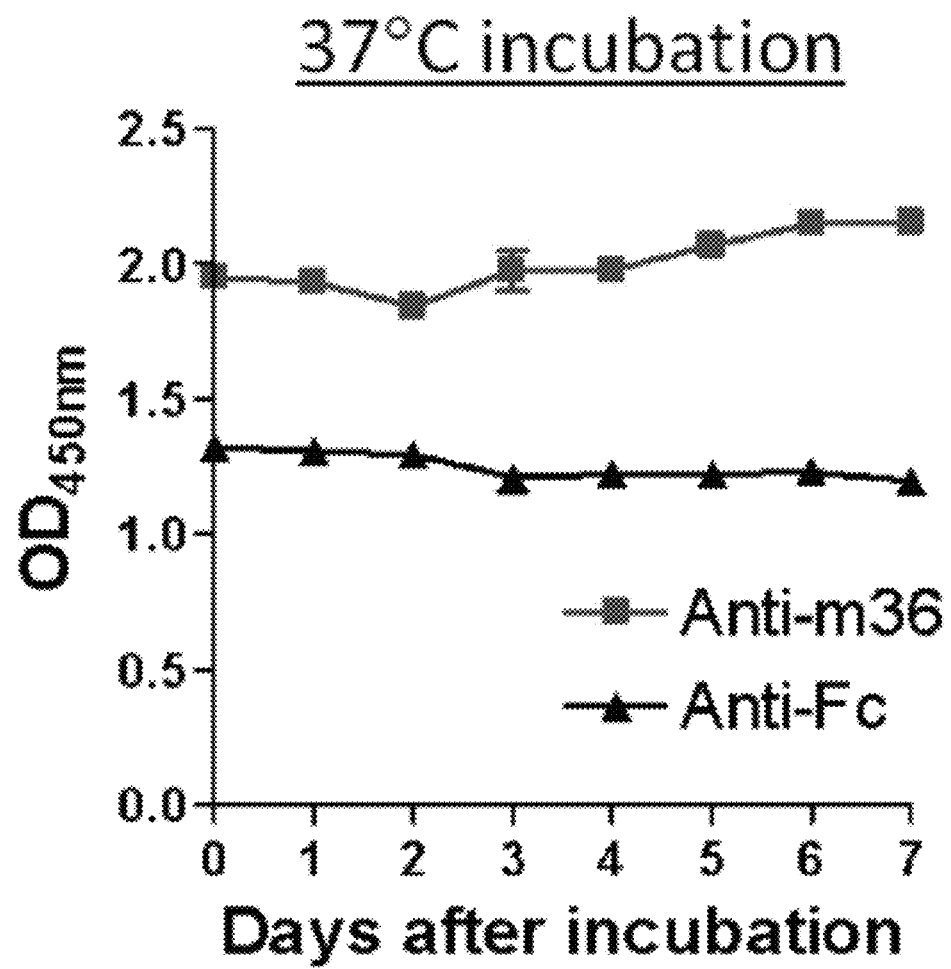

Data from FIG. 10 demonstrates that, over time, there was no loss of CD4 binding as detected by a secondary Ab against iMab Fc, which indicates that the iMab portion of this fusion was still present. The m36 portion of this fusion was also still present as detected by an anti-m36 rabbit immune serum and a secondary Ab against rabbit serum Ig. These results suggest that iMabm36 was stable for up to at least 7 days in the condition tested.

EXAMPLE-2

Construction and Testing of Ibalizumab-PG9

This Example describes the construction and testing of Ibalizumab-PG9 (or also referred to as "PG9-Ibalizumab"), a novel bispecific HIV-1 neutralizing antibody (NAb) for the prevention and treatment of HIV/AIDS. Ibalizumab-PG9 was created as a fusion of the anti-CD4 Ab ibalizumab fused to a single-chain Fv (scFv) version of the anti-HIV envelope NAb, PG9. Ibalizumab-PG9 showed significantly increased antiviral potency and breadth over ibalizumab or PG9 alone. In particular, it potently inhibited viral entry of all ibalizumab-resistant viruses tested. Since ibalizumab and PG9 inhibit HIV entry using two distinct mechanisms, the chance of emerging HIV resistance to the ibalizumab-PG9 fusion is diminished in comparison to either ibalizumab or PG9 alone.

Figure 12:
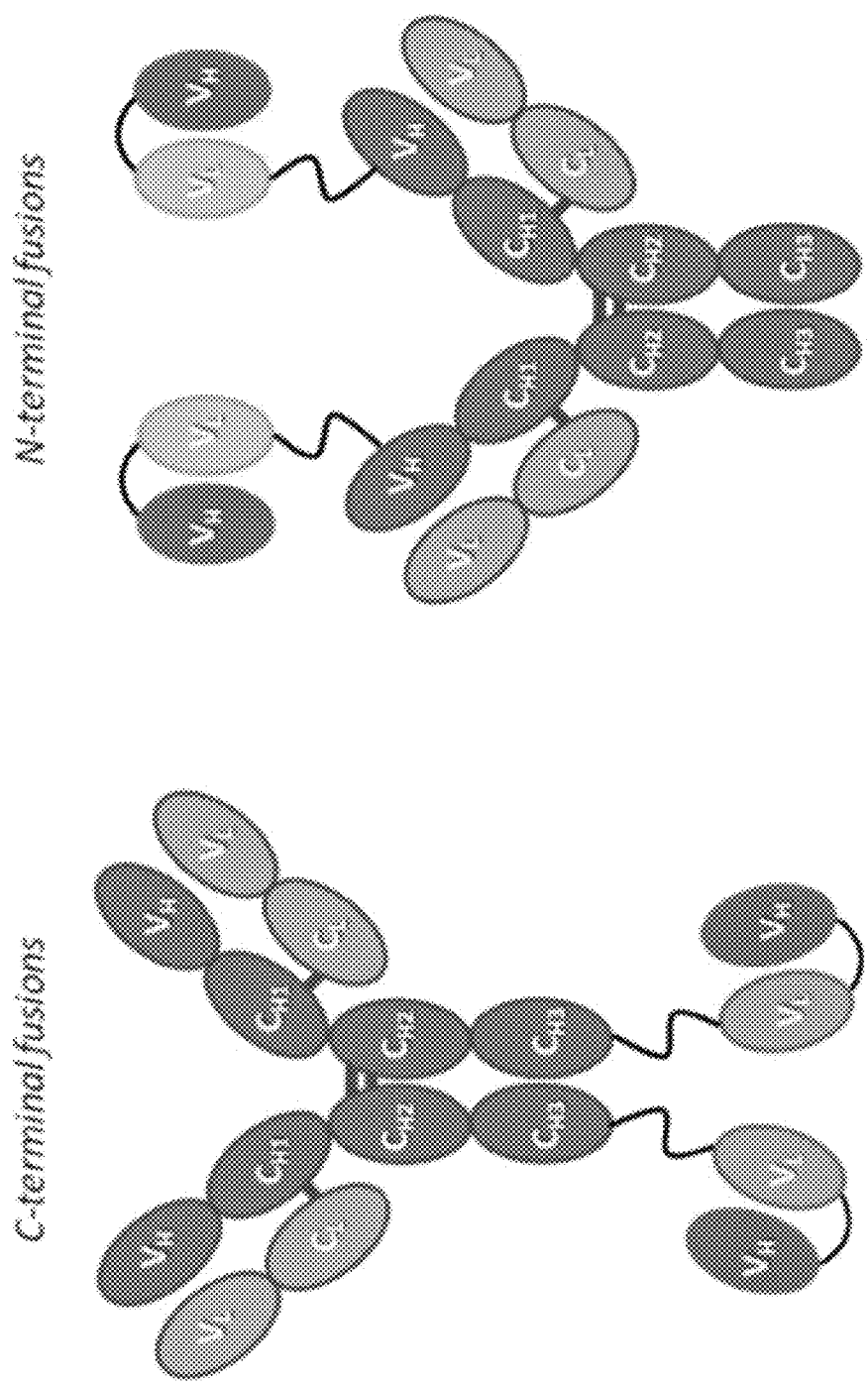

Construction and expression of the ibalizumab-PG9 fusion antibodies. To improve ibalizumab's breadth and potency, bispecific ibalizumab-PG9 was created to simultaneously target both the CD4 receptor on host T-cells and the HIV envelope protein gp120. PG9 is currently one of the most potent and broadest anti-HIV-1 antibodies, targeting a quaternary epitope of the HIV envelope trimer (Walker et al., Science 326, 285-289 (2009)). To create the fusion antibody, the inventors fused the heavy chain variable domain of PG9 to the light chain variable domain of PG9 via a flexible linker (SEQ ID NO: 12) to create a PG9 single chain variable fragment (scFv). This PG9 scFv was then fused via a flexible linker (SEQ ID NO: 14) to the N-terminal and/or C-terminal of the ibalizumab heavy chain to create bispecific ibalizumab-PG9 (FIG. 12). The bispecific fusion antibody with PG9 scFv fused to the N-terminus of the ibalizumab heavy chain (FIG. 15) was used in the following experiments. The Fc region of the ibalizumab of this fusion construct also contained a LALA mutation. The LALA mutation is further described hereinbelow.

Figure 13:
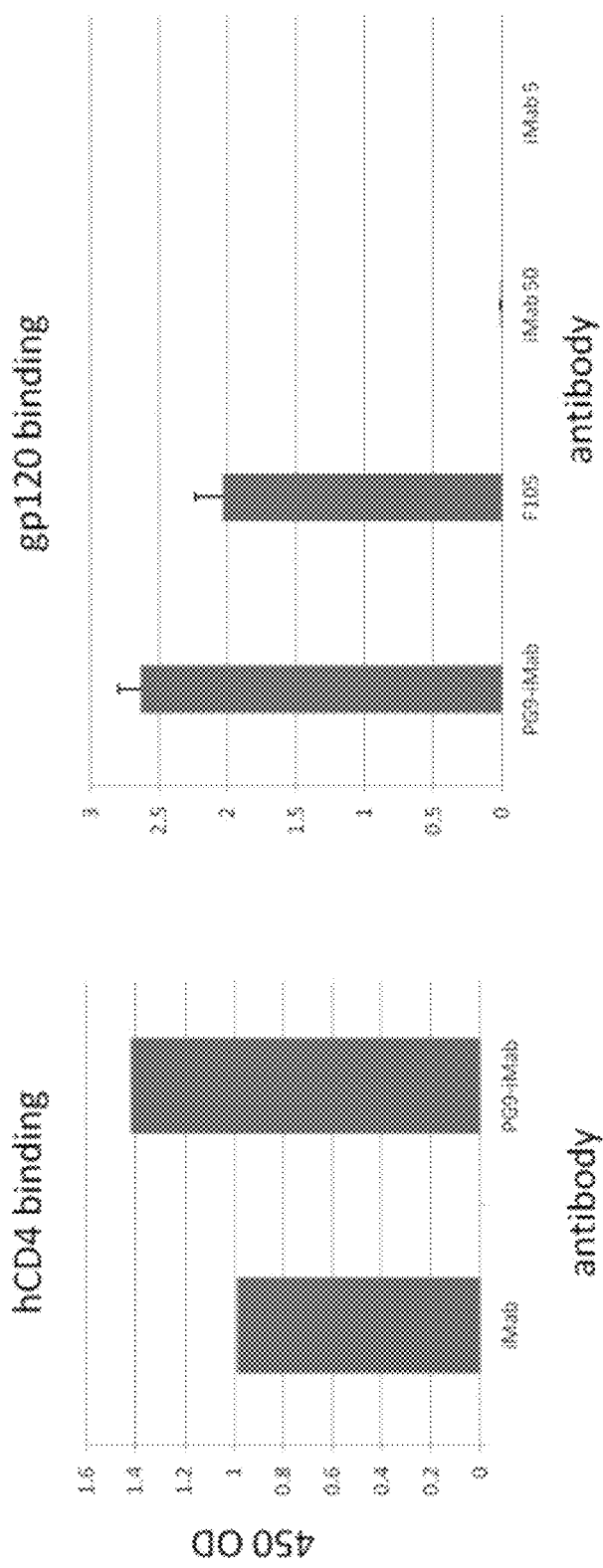

Ibalizumab-PG9 fusion antibody retains its binding functions. The ability of the fusion antibody to bind its cognate antigens was assessed using ELISA. As seen in FIG. 13 (left side), the fusion antibody was able to bind human CD4 comparably to ibalizumab. Biacore studies indicate that the addition of the PG9 scFv had no effect on the affinity at which the antibody binds CD4 (data not shown). To determine if the ibalizumab-PG9 fusion retained the inherent binding activity of PG9, the inventors demonstrated that the fusion antibody was able to bind gp120 comparably to the anti-gp120 antibody F105 (FIG. 13, right side). As expected, ibalizumab was unable to bind gp120, even when tested at concentrations 10-fold higher than that of the fusion antibody.

Figure 14:
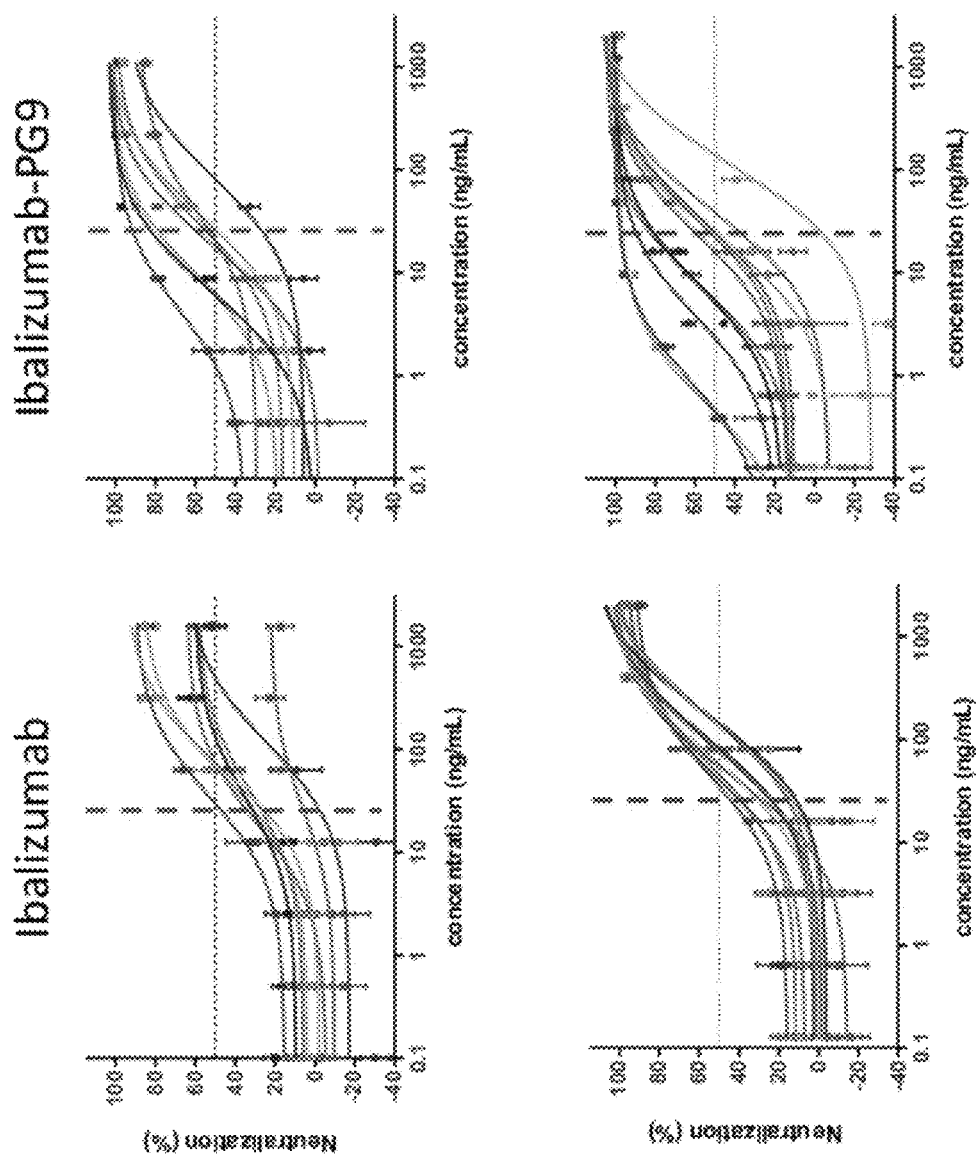

Ibalizumab-PG9 fusion antibody retains and improves virus neutralization activity as compared to ibalizumab alone. To assess the antiviral efficacy of the ibalizumab-PG9 fusion antibody, the inventors determined its HIV-1 neutralization capacity using the standardized single cycle TZM-b1 reporter assay. The ibalizumab-PG9 fusion antibody was able to neutralize 9 out of 9 ibalizumab-resistant viruses to greater than 95% inhibition (FIG. 14, top right). In addition to improving the breadth of ibalizumab, the fusion antibody exhibited significantly enhanced potency (p=0.002), up to 150-fold compared to ibalizumab.

EXAMPLE-3

Construction and Testing of Ibalizumab-VRC01

This Example describes the generation and testing of Ibalizumab-VRC01 (also referred to as "VRC01-Ibalizumab"), a novel bispecific HIV-1 neutralizing antibody (NAb) for the prevention and treatment of HIV/AIDS. Ibalizumab-VRC01 was created as a fusion of a single-chain Fv (scFv) version of the anti-HIV envelope NAb, VRC01, fused to the anti-CD4 Ab ibalizumab. Ibalizumab-VRC01 demonstrated significantly increased antiviral breadth over ibalizumab or VRC01 alone. In particular, it potently inhibited viral entry of all ibalizumab-resistant viruses tested. In addition, complementary resistance to ibalizumab and VRC01 occur via a mutually exclusive genotype. The dominant pathway to ibalizumab resistance involves abrogation of potential N-linked glycosylation (PNG) of the V5 N-terminus. It has been previously demonstrated from a large panel of viruses and from site-directed mutants that the presence of a V5 N-terminal PNG site is sufficient to confer sensitivity to ibalizumab. In contrast, the presence of a V5 N-terminal PNG site substantially reduces (>20-fold) the sensitivity to VRC01. Therefore, combination therapy with ibalizumab and VRC01, either as a fusion antibody or co-administered, is believed to provide a substantially higher genetic barrier to resistance compared to such combinations of any other broadly NAbs against HIV described to date.

Figure 16:
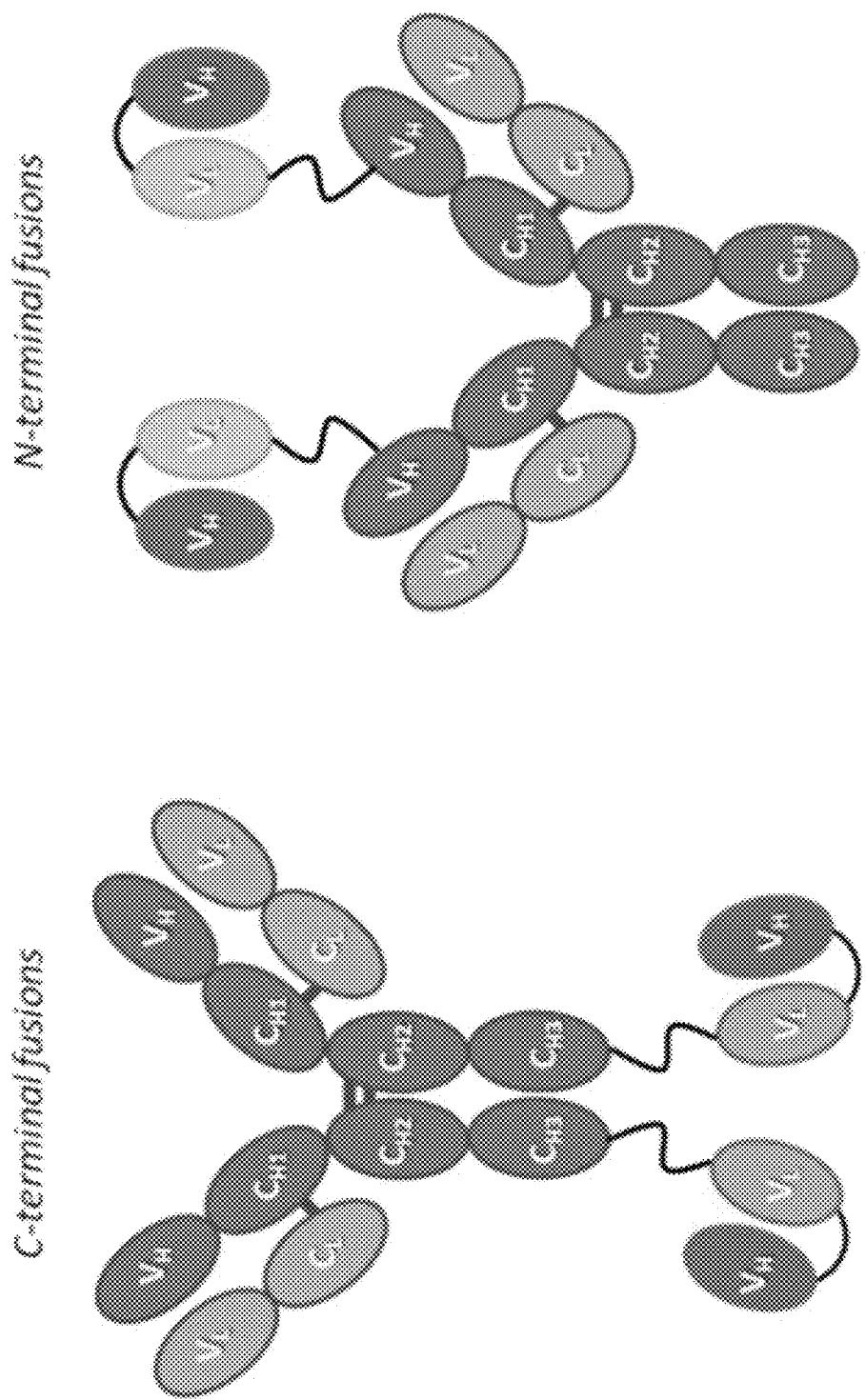

Construction and expression of the ibalizumab-VRC01 fusion antibodies. To improve the breadth of ibalizumab and VRC01, the inventors created bispecific ibalizumab-VRC01 to simultaneously target both the CD4 receptor on host T-cells and the HIV envelope protein gp120. VRC01 is currently one of the most potent and broadest anti-HIV-1 antibodies, targeting the CD4 binding site of the HIV envelope trimer. To create the fusion antibody, the inventors fused the heavy chain variable domain of VRC01 to the light chain variable domain of VRC01 via a flexible (GGGGS)$_4$ (SEQ ID NO: 22) linker to create a VRC01 single chain variable fragment (scFv). This VRC01 scFv was then fused via the flexible (GGGGS)$_4$ (SEQ ID NO: 22) linker to the N-terminal and/or C-terminal of the ibalizumab heavy chain to create bispecific ibalizumab-VRC01 (FIG. 16). The bispecific fusion antibody with VRC01 scFv fused to the N-terminus of the ibalizumab heavy chain (FIG. 19) was used in the following experiments. The Fc region of the ibalizumab of this fusion construct also contained a LALA mutation. The LALA mutation is further described hereinbelow.

Figure 17:
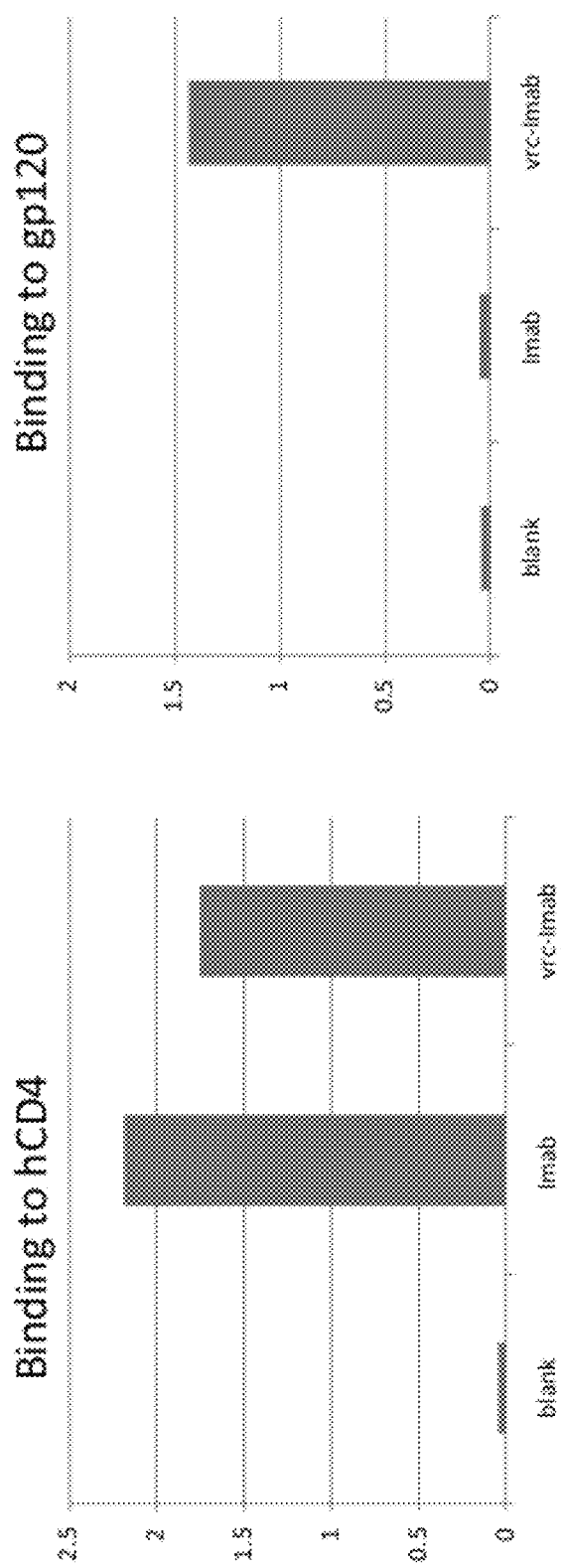

Ibalizumab-VRC01 fusion antibody retains its binding functions. The ability of the fusion antibody to bind its cognate antigens was assessed using ELISA. As seen in FIG. 17 (left side), the fusion antibody was able to bind human CD4 comparably to ibalizumab. To determine if the ibalizumab-VRC01 fusion retained the inherent binding activity of VRC01, the inventors demonstrated that the fusion antibody was able to bind gp120 (FIG. 17, right side). As expected, ibalizumab alone was unable to bind gp120.

Figure 18:
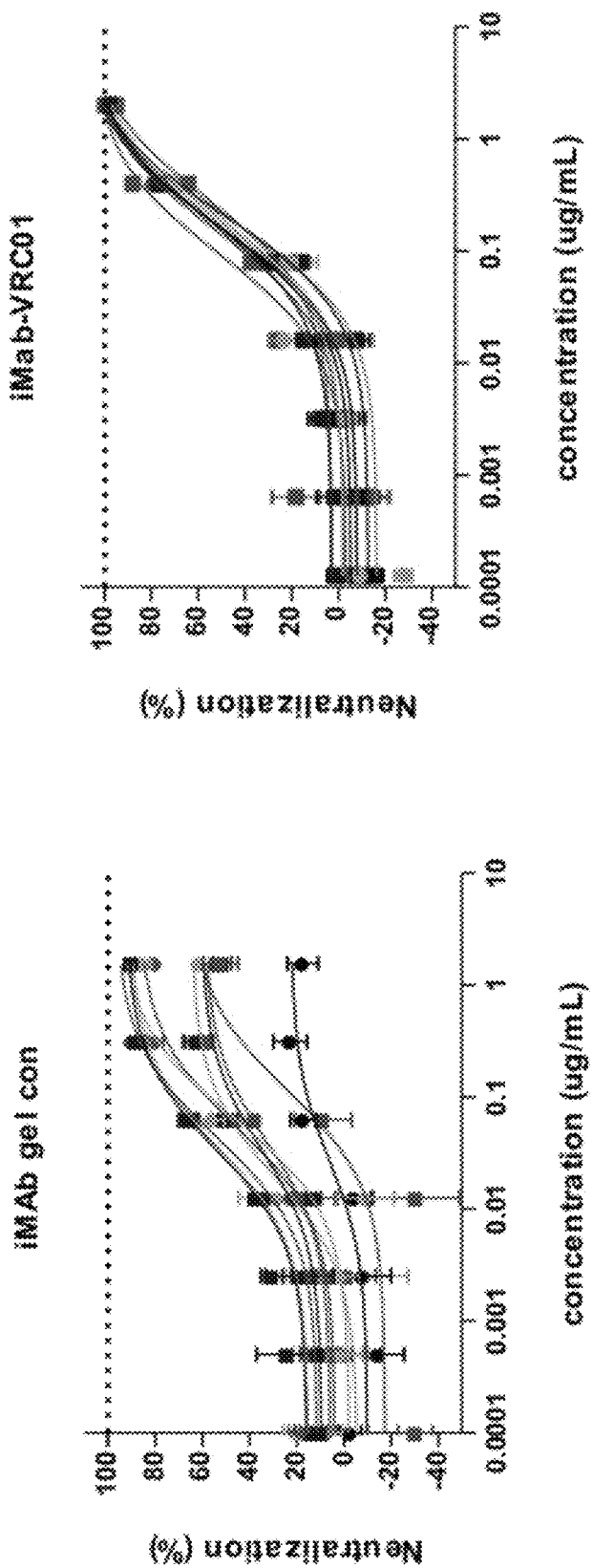

Ibalizumab-VRC01 fusion antibody retains and improves virus neutralization activity as compared to ibalizumab alone. To assess the antiviral efficacy of the ibalizumab-VRC01 fusion antibody, the inventors determined its HIV-1 neutralization capacity using the standardized single cycle TZM-b1 reporter assay. The ibalizumab-VRC01 fusion antibody was able to neutralize 10 out of 10 ibalizumab-resistant viruses to 100% inhibition (FIG. 18, right).

EXAMPLE-4

Improvements of Bispecific Fusion Antibodies Over Ibalizumab In Breadth and Potency The improvement of the fusion antibodies constructed herein as compared to ibalizumab is illustrated as follows.

Figure 20:
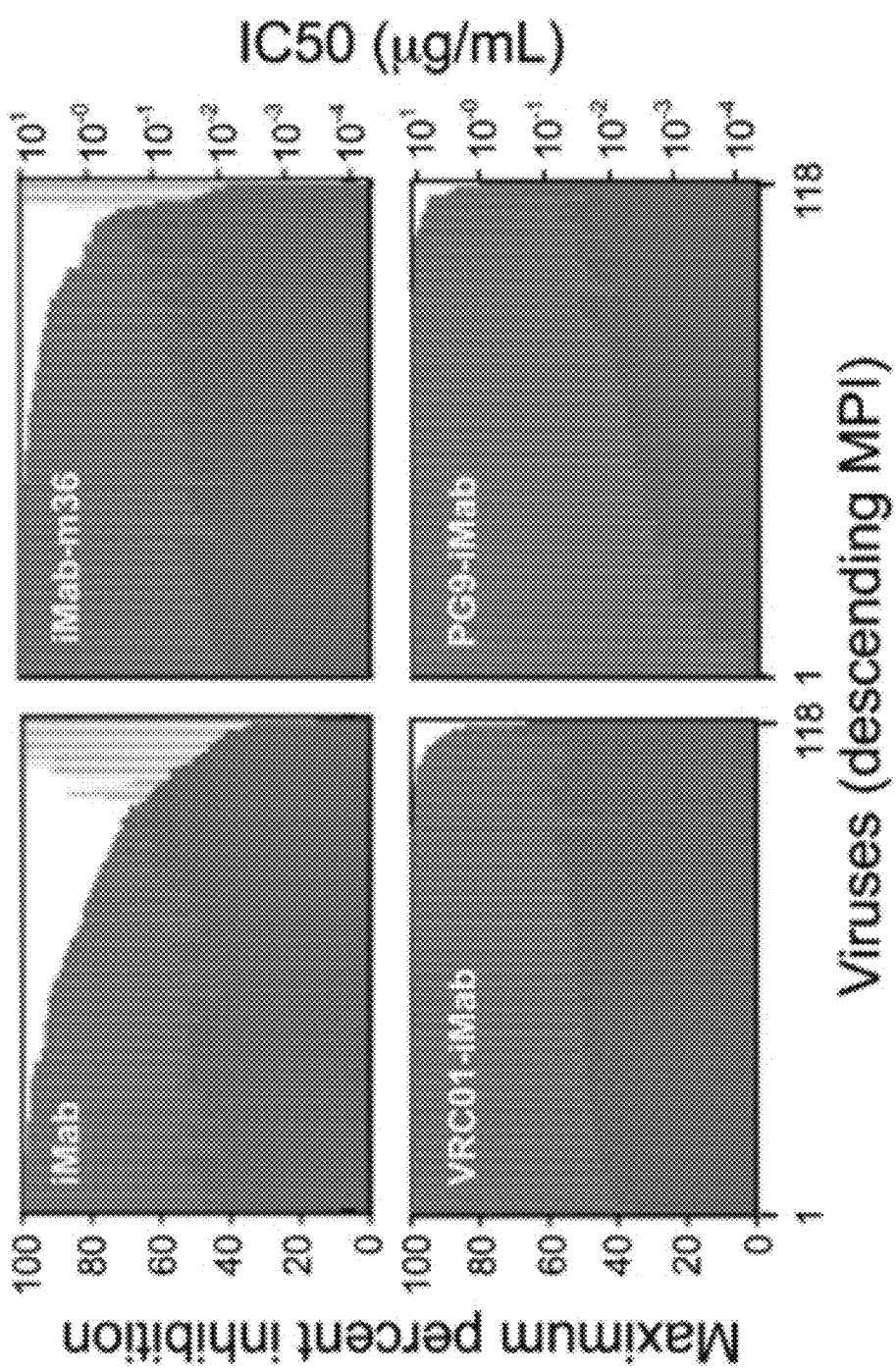

The top-left panel of FIG. 20 recapitulates the in vitro neutralizing activity of unmodified ibalizumab (iMab) against a panel of 118 HIV isolates, illustrating the "hole" in its repertoire. An IC50 of ≥10 ug/mL was noted for a small fraction of the viruses, but high-level neutralization (MPI>80%) was not achieved for many more viruses. iMab-m36 (Example 1) demonstrated a modest increase in breadth (top-right, FIG. 20). VRC01-iMab (Example 3) showed even greater breadth and potency with IC50s consistently between 0.01 and 0.1 µg/mL (bottom-left). Most notable were the neutralizing activities exhibited by PG9-iMab (Example 2) (bottom-right), where breadth of 100% (as measured by ≥80% neutralization) was observed, as was a significant increase (>200-fold by IC90) in potency (median IC50, IC90 and IC99 of 0.005 µg/mL, 0.028 µg/mL, and 0.080 µg/mL, respectively).

Figure 21:
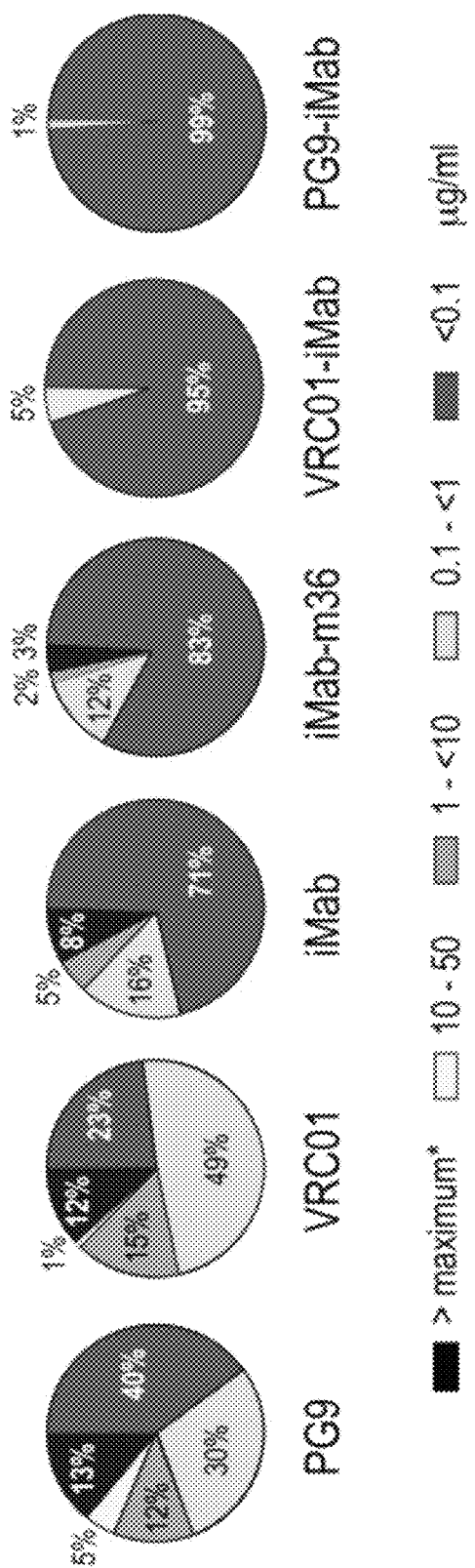

The remarkable gain in anti-HIV activity of the fusion antibodies is even more evident when shown as percentage coverage of viruses neutralized over a range of concentrations (FIG. 21). In particular, 99% of the viruses were neutralized by PG9-iMab at concentrations <0.1 µg/mL.

Figure 22:
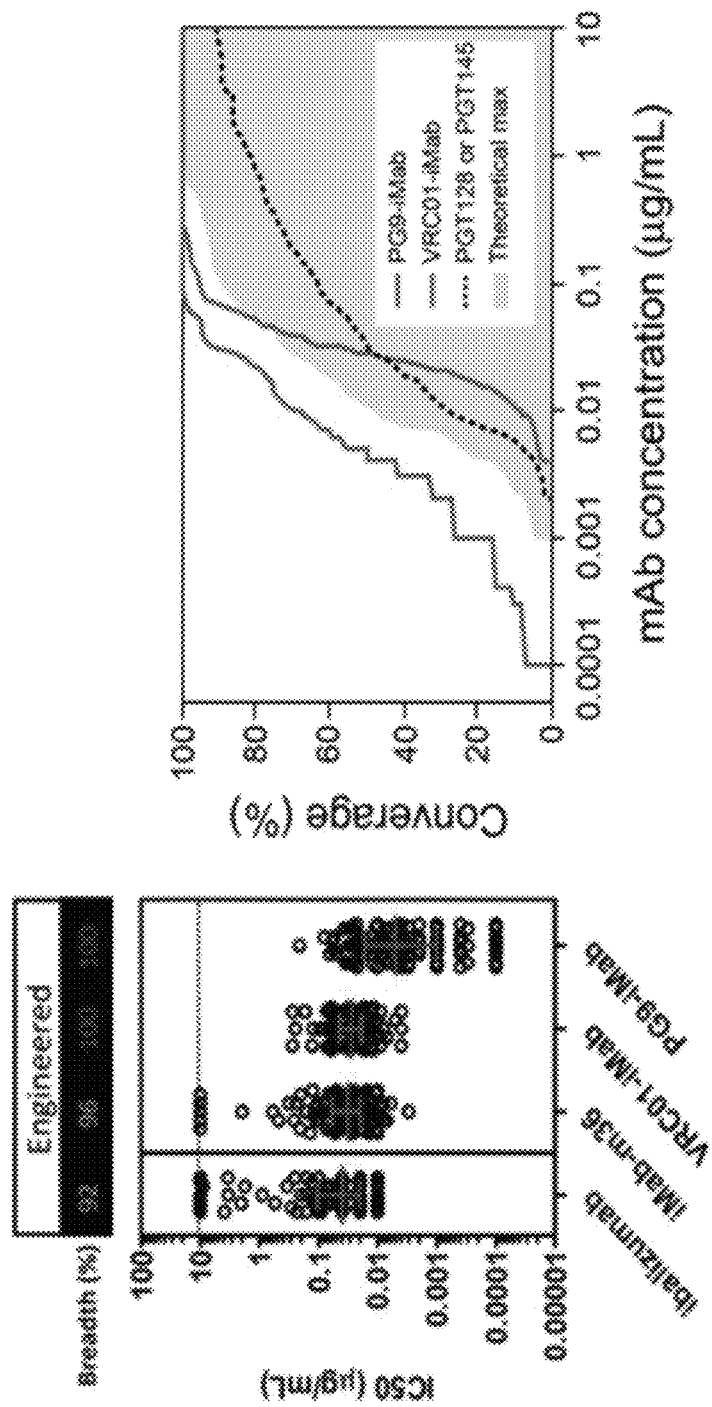

The antiviral potency of the bispecific antibodies was also displayed by showing their IC50s on a scattered plot in comparison with results for ibalizumab (FIG. 22). The improvement is readily evident.

EXAMPLE-5

PK Improvements on the Ibalizumab Backbone

Figure 23:
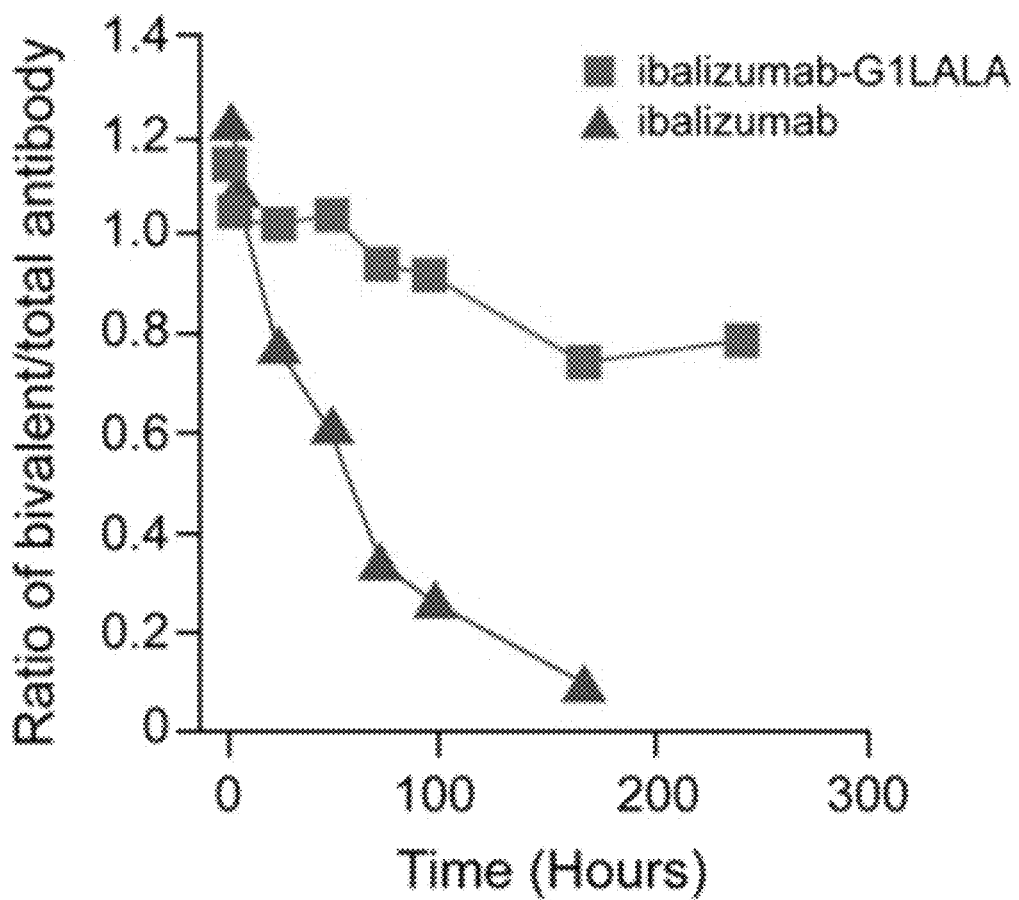

Ibalizumab has a relatively short half-life in vivo (3.5 days for IV administration and ~10 days for SC administration). mAbs humanized with IgG4 (such as ibalizumab) are known to have a strong tendency to switch their inter-chain disulfide bonds to intra-chain disulfide bonds, resulting in the dissociation of the antibody into monomers. In order to improve stability, the Fc region of the ibalizumab was modified to introduce the so-called "LALA" (Leu to Ala and Leu to Ala) mutations. The Fc regions of PG9-ibalizumab (FIG. 15) and VRC01-ibalizumab (FIG. 19) each contained a set of LALA mutations ((Leu to Ala and Leu to Ala). In an additional construct, the ibalizumab backbone was modified by replacing IgG4 with human IgG1 carrying the LALA mutations (L234A/L235A) (Hessell et al., Nature 449(7158): 101-4, 2007) that reduced effector function mediated through FcRs (with exception of FcRn, see below). The particular "LALA" modifications made in this additional construct are L239F, L240E (the numbering system does not account for the 19 amino acid leader sequence) and correspond to position 258 and 259 of SEQ ID NO: 30. When infused into rhesus monkeys in short-term experiments, this new variant was more stable by about 5-fold relative to ibalizumab (FIG. 23).

Figure 24:
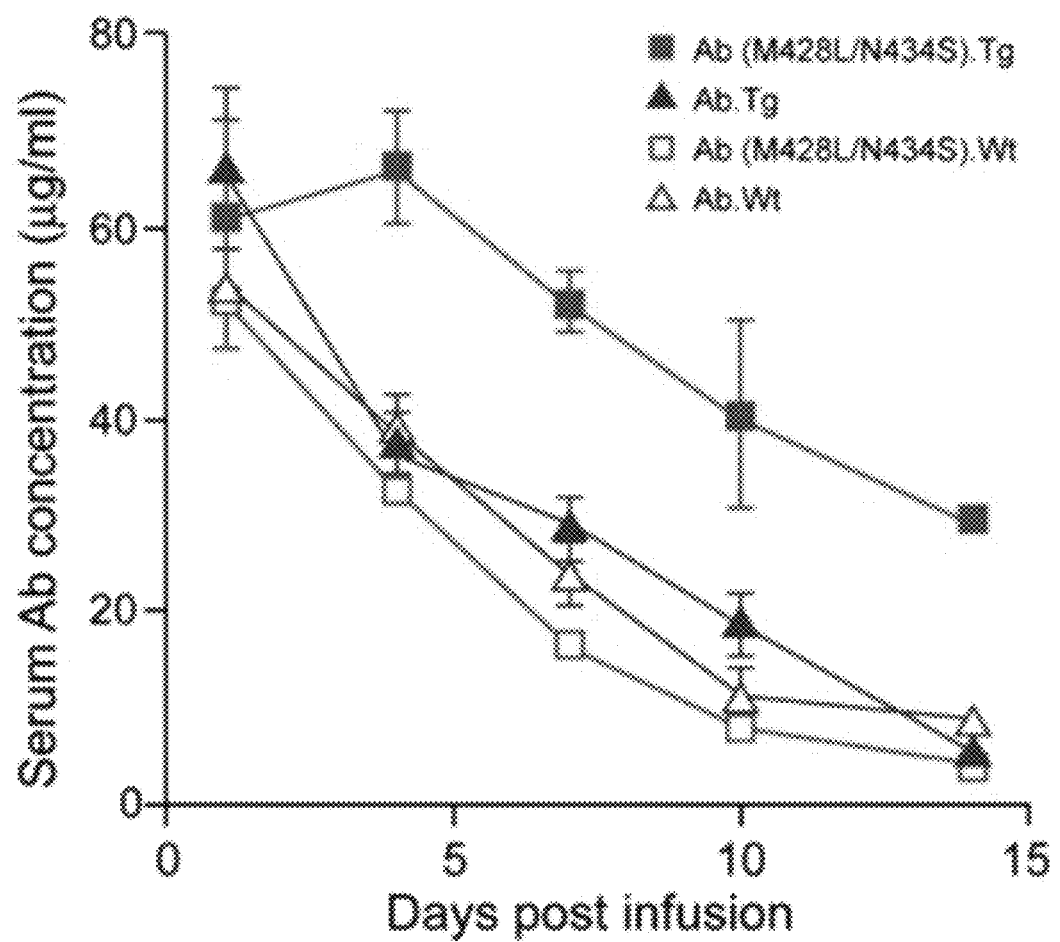

In addition, the inventors also modified the backbone of ibalizumab in order to increase the recycling of ibalizumab via the antibody salvage pathway. FcRn, the so-called neonatal FcR, has been shown to be involved in the transcytosis of IgG across epithelium, allowing transfer of maternal antibodies to the fetus (Ghetie et al., Immunol. Res. 25(2):97-113, 2002). Considerable evidence exists to support the additional role of FcRn in regulating levels of circulating IgG (Roopenian et al., Nat. Rev. Immunol. 7(9):715-25, 2007). Serum IgG is taken up by endothelial cells into their endosomes via fluid-phase pinocytosis. Typically, the Fc region of IgG binds FcRn only at pH 6.0-6.5 (endosomes), while dissociation of the IgG-FcRn complex is facilitated at pH 7.0-7.4 (cell surface). Therefore, upon acidification within endosomes, IgG binds to FcRn, which is then recycled to the cell surface and released from FcRn. IgG molecules that are not bound to FcRn within the endosomes are degraded. FcRn thus functions as a salvage receptor, rescuing IgG from the lysosomal degradation pathway. Therefore, manipulations to enhance the IgG-FcRn interaction could improve the PK of a mAb in vivo. Indeed, it has been reported that M428L/N434S mutations have beneficial effects on PK (Zalevsky et al., Nat. Biotechnol. 28(2):157-9, 2010). With this combination of mutations, affinity for FcRn at pH 6.0 increased by 11-fold, largely due to a slower off rate. When placed into the context of bevacizumab (Avastin, IgG1, anti-VEGF, approved for treatment of colon, lung, and breast cancer) or cetuximab (Erbitux, IgG1, anti-EGFR, approved for treatment of colon and head and neck cancers), the PK profile of both antibodies improved by 5-fold in human FcRn transgenic mice and by 3-fold in cynomolgus monkeys. The inventors made this set of mutations (M433L, N439S) in the IgG1-LALA version of ibalizumab (the numbering system does not account for the 19 amino acid leader sequence), which correspond to positions 452 and 458, respectively of SEQ ID NO: 30. This modification led to a ~3-fold improvement in PK in human-FcRn-transgenic mice versus wild-type mice (FIG. 24).

SEQ ID NO: 30 sets forth the amino acid sequence of iMabm36 heavy chain with the modifications discussed above. Residues 1-19 of SEQ ID NO: 30 constitute a leader sequence (SEQ ID NO: 10); residues 20-471 represent the iMab heavy chain with IgG1-LALA and FcRn mutations (SEQ ID NO: 31); residues 472-489 represent a linker (SEQ ID NO: 32), and residues 490-606 represent m36 variable heavy chain (SEQ ID NO: 4).

EXAMPLE-6

Figure 25:
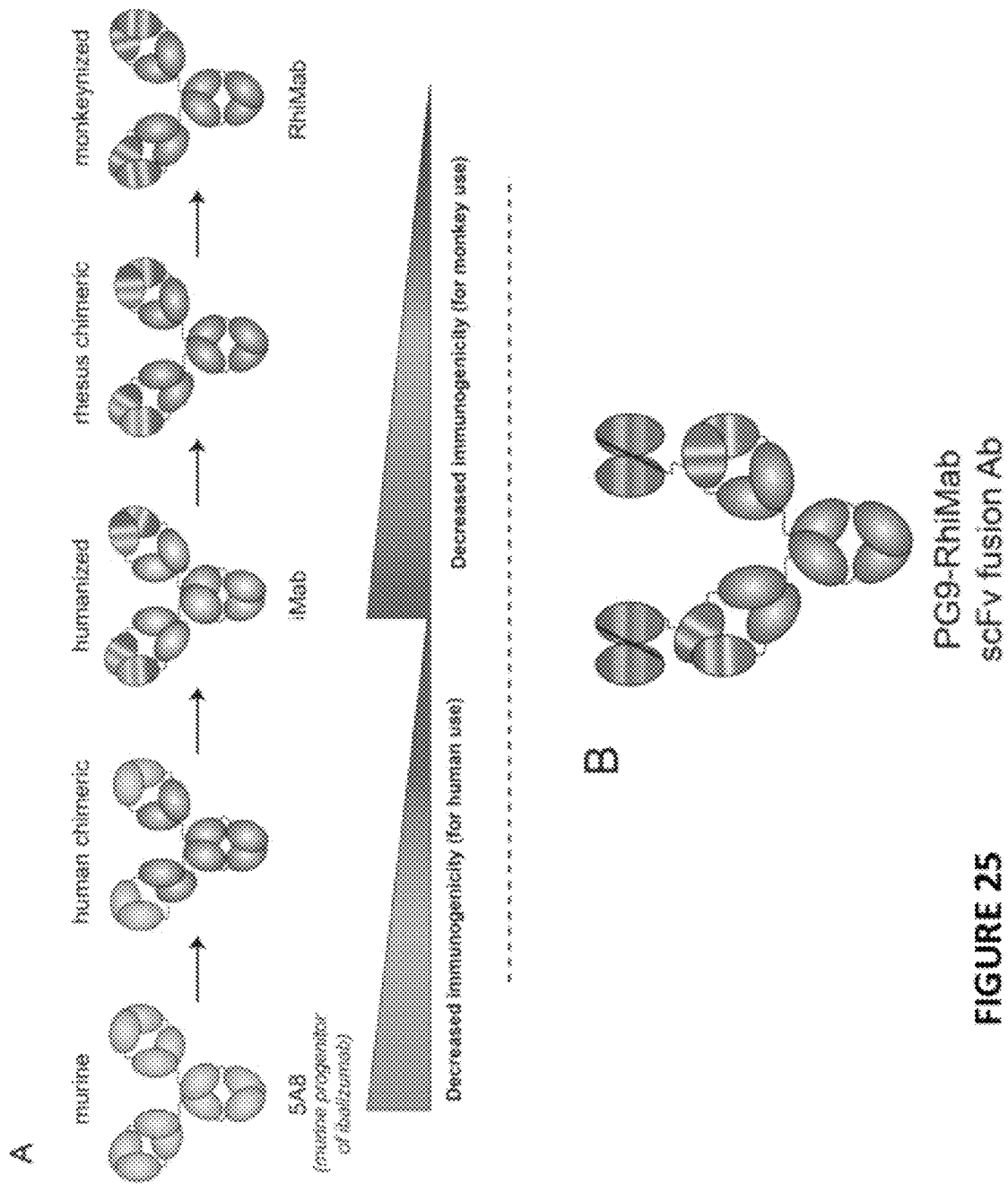

PK Evaluation, Immunogenicity Assessment, and SHIV Prevention Studies in Monkeys Bispecific fusion antibody candidates with the desired antiviral and PK properties as determined by in vitro assessment of the binding affinity for both CD4 and gp120 are further assessed in vivo in rhesus macaques. However, to avoid the immunogenicity of the humanized antibody molecules in monkeys, rhesus equivalents of the bispecific humanized antibodies were generated. For example, for ibalizumab containing the PK enhancement mutations (G1-LALA and M428L/N434S), the CH1, CH2, and CH3 domains were first replaced with their rhesus counterparts, as depicted in FIG. 25A. Such a chimeric construct could still have a high probability of being immunogenic in monkeys because of the "human" framework residues in the Fv region. Thus, these framework residues were systematically replaced with rhesus amino acids, thereby creating a full "monkeynized" version of the antibody, which was called RhiMab (depicted in FIG. 25A). During this process, care was taken to avoid any loss in the antigen-binding property of the antibody. More specifically, based on the sequence alignment of iMab with GenBank available IgG of rhesus macaque sequences, a total of 8 amino acid residues (3 from heavy chain and 5 from light variable regions) of iMab were identified. All eight amino acid residues and combinations thereof were substituted with amino acids that were conserved in rhesus IgG. The amino acid sequences of the heavy and light chains of one of the resulting antibodies (RhiMab) are shown in FIG. 26 A. RhiMab was functionally characterized by a) sCD4 competition binding ELISA, 2) BiaCore binding, and 3) and a viral neutralization activity assay.

The PK profile of RhiMab in monkeys is determined as follows. A range of doses (from 1 mg/kg to 10 mg/kg) of this antibody is administered SC to macaques. Blood is drawn serially in the ensuing month to measure the serum level of the antibody over time. PBMCs are isolated to assess the percentage of CD4 receptors on T-cells bound by the antibody, and the resultant receptor occupancy values are correlated with serum antibody concentrations. Rectal and cervico-vaginal (if available) biopsies are obtained one week after RhiMab administration to quantify the extent of antibody coating of mucosal CD4 T-cells. It is crucially important to have adequate antibody penetration into these mucosal sites, through which HIV enters a new host. Three additional SC doses of RhiMab are given to each monkey at 1, 2, and 3 months following the initial injection. Again serial blood samples are drawn to determine whether there is accumulation of antibody over repeated dosing as well as to evaluate changes in the PK profile or receptor occupancy values during chronic administration. During this latter period, mucosal biopsies are only performed sparingly, as dictated by the PK findings.

An unusually low PK profile could hint at the development of an immunogenic response. An assay is currently under development to detect anti-RhiMab antibodies in macaque serum over time. A negative result would confirm that the RhiMab scaffold on which to build the bispecific constructs was indeed non-immunogenic. If immunogenicity is a frequent occurrence, attempts will be made to map the site(s) on RhiMab that is (are) responsible for inducing an antibody response. Once defined, substitutions at the site(s) on RhiMab would be made with the hope of eliminating the immunogenic potential.

PG9 scFv was selected for conversion into the rhesus equivalents. Specifically, amino acids in human PG9 scFv were identified based on the conserved amino acid usage in a panel of rhesus macaque antibody sequences found from GenBank. A total of 19 amino acid residues (14 from heavy chain and 5 from light chain) were identified and changed to generate rhesus PG9 scFv. The sequences of the heavy and light chains of the rhesus PG9 scFv are shown in FIG. 26B.

A bispecific fusion was then created with rhesus PG9 scFv and RhiMab, as shown in FIG. 25B. The bispecific antibody is tested in an initial PK study in monkeys similar to those already described. A dose is then chosen based on the maintenance for 2 months of serum levels above the IC90 and/or high receptor occupancy. At week 0, the antibody is administered SC to six rhesus macaques, while six additional animals serve as untreated controls. Each antibody is given again at the same dose SC at week 8 and week 16. Beginning on day 4, all monkeys are challenged intrarectally (IR) with low-dose SHIV. The IR inoculations are repeated weekly for 11 more times. All animals are monitored frequently over 6 months for seroconversion, plasma viremia, CD4 cell counts, and clinical manifestations of immunodeficiency. Protection conferred by the bispecific antibodies are scored by three different measures. First is complete protection against SHIV infection; second is the number of extra viral inoculations needed to achieve infection; and the third is an attenuation of infection as reflected by low viral loads, high CD4 cell counts, and lack of disease progression.

EXAMPLE-7

Affinity Maturation to Alter the Fab Binding Recognition Region of Ibalizumab

Random mutations were generated in CDR residues chosen on the basis of the structure information from the ibalizumab-CD4 complex. A standard yeast display screening system was utilized to identify variants with higher or lower affinities. Guided by structural information, random mutations were introduced at specified positions within the CDRs to generate a single-chain Fv (scFv) library. Variants in the library were then transformed into yeast and subsequently expressed on the cell surface. Human soluble CD4 (sCD4) was used to bind cells expressing scFv in competition with unmodified scFv. CD4 binding was detected by staining with an anti-CD4 antibody followed by secondary detection reagents. The binding signal was measured by flow cytometry and the higher affinity CD4 binding clones were isolated by fluorescent-labeled cell sorting. The N-terminal c-myc epitope tag on scFv was also simultaneously stained by a second color with an anti-c-myc antibody in order to ensure that the full-length scFv expressed clones were properly separated by cell sorting. Selected clones were grown again and assessed for higher affinity CD4 binding in multiple rounds of selection to ensure enrichment of the highest affinity forms. After the final round of selection, the best yeast clones were isolated and their respective scFvs were subjected to DNA sequencing in order to identify the mutations present.

Figure 27:
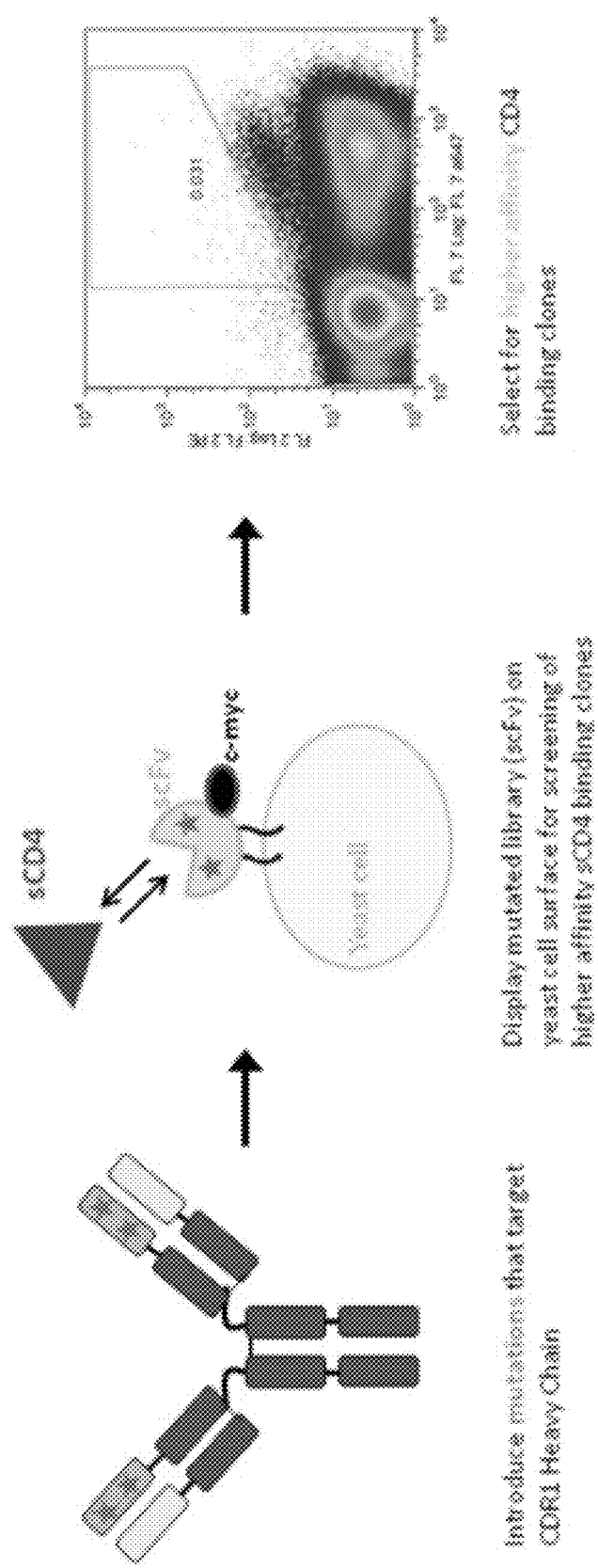

FIG. 27 is a schematic summary of the method used to conduct "in vitro affinity maturation". Example shown therein is for mutations directed to CDR-H1, but a similar approach was taken for other CDRs.

Higher affinity forms were generated, including one CDR-H1 variant of ibalizumab that has a 12.5-fold improvement in affinity (KD of 10 pM) (Table 1). iMab mutants tested by yeast platform demonstrated increased or decreased affinity to CD4 (Table 2). Variants with the highest and lowest affinity were confirmed by Biacore (Table 3).

TABLE 1

Affinity improvement after 2 rounds of screening - tested by yeast display platform

|  | CDR-H1 | | | | | clone | $K_D$ | Fold improvement in affinity compare to wt iMab scFv | SEQ ID NOS |
|---|---|---|---|---|---|---|---|---|---|
| 2nd round Library | T | S | Y | V | I | H |  |  |  | 36 |
|  | T | S | Q | T | I | H | 23 | 19.2 | 6.3 | 37 |
|  | T | S | Q | T | L | H | 33 | 12 | 10.1 | 38 |
|  | T | A | Q | T | I | H |  |  |  | 39 |
|  | T | A | Q | T | L | H | 30 | 10.7 | 11.4 | 40 |
|  | T | E | Q | T | L | H | 24, 35 | 9.7 (9.2; 10.2) | 12.5 | 41 |
|  | T | D | Q | T | L | H | 27, 31 | 15 (15.8; 14.3) |  | 42 |
|  | T | D | Q | T | M | H |  |  |  | 43 |
|  | T | G | Q | T | L | H | 25, 37 | 17.3 (16; 18.7) | 7 | 44 |
|  | T | N | Q | T | L | H | 26, 36 | 40.6 (48.9; 38.2) | 3 | 45 |
|  | T | N | Q | V | I | H |  |  |  | 46 |
|  | T | D | Y | T | F | H | 28 | 13.2 | 9.2 | 47 |
|  | T | E | Y | T | F | H | 40 | 11.2 | 10.9 | 48 |
| 1st round clone | T | D | Y | T | I | H | 22 | 34.6 | 3.5 | 49 |
| control | T | S | Y | V | I | H | wt, 28 | wt control 121.6 (118.6; 124.6) |  | 36 |

TABLE 2

Affinity tested by yeast platform for increased or decreased iMab mutants

| Mutants | sequence | Yeast $K_D$ (pM) | SEQ ID NOS |
|---|---|---|---|
| M24 | EQTLH | 9.7 | 50 |
|  | AQTLH | 10.7 | 51 |
|  | EYTFH | 11.2 | 52 |
|  | SQTLH | 12 | 53 |
|  | DYTFH | 13.2 | 54 |
|  | DQTLH | 15 | 55 |
|  | SQTIH | 19.2 | 56 |
|  | DYTIH | 34.6 | 57 |
| wt CDR-H1 | SYVIH | 121.6 | 58 |
| ML1 | SRVLS | 2128 | 59 |
| (wt CDR-H3) | AREKDNYATGAWFA |  | 60 |
| ML28 | AREKDNYAVPGWFA | 1406 | 61 |
| ML29 | AREKDSLTTGAWFA | 2230 | 62 |
| ML11 | VREKDSFATGAWFA | 2468 | 63 |
| ML26 | ARQAANYATGAWFA | 3643 | 64 |

TABLE 3

Affinity tested by Biacore for increased or decreased iMab mutants

| Mutants | sequence | $K_D$ (pM) | Kon (1/Ms) | Koff (1/s) |  | SEQ ID NOS |
|---|---|---|---|---|---|---|
|  |  | Biacore (T100) | | | | |
| M24 | EQTLH | 4.2 | $0.68 \times 10^6$ | $0.028 \times 10^{-4}$ |  | 50 |
| wt CDR-H1 | SYVIH | 150 | $1.37 \times 10^6$ | $2.06 \times 10^{-4}$ |  | 58 |
| ML1 | SRVLS | 2142 | $0.35 \times 10^6$ | $7.5 \times 10^{-4}$ | By Biacore-T100 | 59 |
|  |  | Biacore $K_D$ (pM) | | | | |
| M28 | DYTFH | 14 | $0.28 \times 10^6$ | $0.04 \times 10^{-4}$ |  | 54 |
| M24 | EQTLH | 18 | $0.28 \times 10^6$ | $0.05 \times 10^{-4}$ |  | 50 |
| M3 | EYTIH | 33 | $1 \times 10^6$ | $0.32 \times 10^{-4}$ |  | 65 |
| M22 | DYTIH | 47 | $1.5 \times 10^6$ | $0.71 \times 10^{-4}$ |  | 57 |
| wt (in-house) |  | 430 | $0.28 \times 10^6$ | $1.2 \times 10^{-4}$ | By Biacore-3000 |  |
| (wt CDR-H3) | AREKDNYATGAWFA | 150 | $1.37 \times 10^6$ | $2.06 \times 10^{-4}$ |  | 60 |
| ML28 | AREKDNYAVPGWFA | 1759 | $0.734 \times 10^6$ | $13.18 \times 10^{-4}$ |  | 61 |
| ML26 | ARQAANYATGAWFA | 4143 | $1.6 \times 10^6$ | $66.3 \times 10^{-4}$ |  | 64 |
| ML29 | AREKDSLTTGAWFA | 4829 | $0.94 \times 10^6$ | $45.4 \times 10^{-4}$ |  | 62 |
| ML11 | VREKDSFATGAWFA | 6722 | $0.839 \times 10^6$ | $56.4 \times 10^{-4}$ | By Biacore-T100 | 63 |
| E95A | ARAKDNYATGAWFA | 7700 | $0.62 \times 10^6$ | $48 \times 10^{-4}$ | By Biacore-3000 | 66 |

What is claimed is:

1. A fusion antibody, comprising a first antigen-binding site which binds to the D1 domain, D2 domain or D1-D2 junction of the CD4 receptor, conjugated to a second antigen-binding site which binds to an epitope on HIV gp120 envelope.

2. The fusion antibody of claim 1, comprising an intact anti-CD4 antibody or a fragment thereof which provides said first antigen-binding site, conjugated to an anti-HIV gp120 envelope antibody or a fragment thereof which provides said second antigen-binding site.

3. The fusion antibody of claim 2, wherein said anti-CD4 antibody is humanized or monkeynized.

4. The fusion antibody of claim 2, wherein said anti-CD4 antibody is ibalizumab or a derivative thereof.

5. The fusion antibody of claim 2, wherein said anti-CD4 antibody is an affinity matured antibody that has a greater binding affinity to CD4 than ibalizumab.

6. The fusion antibody of claim 1, wherein said HIV gp120 envelope is on a HIV gp120 trimer or monomer.

7. The fusion antibody of claim 1, wherein said epitope on the HIV gp120 envelope is (i) CD4-bridging sheet site on HIV gp120, (ii) CD4 binding site on HIV gp120, or (iii) V1+V2/V3 regions of HIV gp120 trimer.

8. The fusion antibody of claim 2, wherein said anti-HIV gp120 envelope antibody binds to a quaternary epitope on the HIV gp120 trimer.

9. The fusion antibody of claim 2, wherein said anti-HIV gp120 envelope antibody binds to V1/V2 and V3 regions of HIV gp120 trimer.

10. The fusion antibody of claim 9, wherein said anti-HIV gp120 envelope antibody is PG9.

11. The fusion antibody of claim 2, wherein said anti-HIV gp120 envelope antibody binds to a CD4-bridging sheet site-on HIV gp120.

12. The fusion antibody of claim 11, wherein said anti-HIV gp120 envelope antibody is m36.

13. The fusion antibody of claim 2, wherein said anti-HIV gp120 envelope antibody binds to CD4 binding site on HIV gp120.

14. The fusion antibody of claim 13, wherein said anti-HIV gp120 envelope antibody is VRC01.

15. The fusion antibody of claim 2, wherein the anti-CD4 envelope antibody is modified in the Fc region to introduce human IgG 4 or IgG1 carrying the LALA mutations.

16. The fusion antibody of claim 2, wherein the anti-CD4 antibody is additionally modified in the FcRn region to include one or more mutations that improve recycling of the anti-CD4 antibody.

17. A method of treating a subject infected with HIV comprising administering to the subject a therapeutically effective amount of the fusion protein according to any one of claims 1-16.

18. A method of inhibiting HIV infection in a subject in need thereof comprising administering to the subject a therapeutically effective amount of the fusion protein according to any one of claims 1-16.

19. A method of inhibiting a HIV-positive pregnant subject from transmitting the HIV virus to the child, comprising administering to the subject a therapeutically effective amount of the fusion protein according to any one of claims 1-16.

20. A fusion antibody, comprising a first antigen-binding site which binds to the D1, D2 domain or D1-D2 junction of the CD4 receptor, conjugated to a second antigen-binding site which binds to (i) CD4-bridging site on HIV gp120, (ii) CD4 binding site on HIV gp120, or (iii) V1+V2/V3 regions of HIV gp120 timer.

21. The fusion antibody of claim 20, wherein the first antigen-binding site which binds to the D2 domain or D1-D2 junction of the CD4 receptor.

22. The fusion antibody of claim 20, comprising ibalizumab or a derivative thereof, conjugated to a second antigen-binding site which binds to (i) CD4 bridging sheet site on HIV gp120, (ii) CD4 binding site on HIV gp120, or (iii) V1+V2V3 regions of HIV gp120 timer.

23. The fusion antibody of claim 21, comprising ibalizumab or a derivative thereof, conjugated to a second antigen-binding site which binds to (i) CD4 bridging sheet site on HIV gp120, (ii) CD4 binding site on HIV gp120, or (iii) V1+V2V3 regions of HIV gp120 timer.

24. A fusion antibody, comprising ibalizumab or a derivative thereof, conjugated to m36 or an antigen-binding fragment thereof.

25. A fusion antibody, comprising ibalizumab or a derivative thereof, conjugated to PG9 or an antigen-binding fragment thereof.

26. A fusion antibody, comprising ibalizumab or a derivative thereof, conjugated to VRC01 or an antiagen-binding fragment thereof.

27. The fusion antibody of claim 2, wherein said first antigen-binding site binds to the D1 domain of the CD4 receptor.

28. The fusion antibody of claim 2, wherein said first antigen-binding site binds to the D2 domain of the CD4 receptor.

29. The fusion antibody of claim 2, wherein said first antigen-binding site binds to the D1-D2 junction of the CD4 receptor.

* * * * *

SEQUENCE LISTING

<160> NUMBER OF SEQ ID NOS: 68

<210> SEQ ID NO 1
<211> LENGTH: 606
<212> TYPE: PRT

<213> ORGANISM: Artificial Sequence
<220> FEATURE:
<223> OTHER INFORMATION: An iMabm36 fusion protein

<400> SEQUENCE: 1

```
Met Glu Trp Ser Gly Val Phe Met Phe Leu Leu Ser Val Thr Ala Gly
1               5                   10                  15

Val His Ser Gln Val Gln Leu Gln Gln Ser Gly Pro Glu Val Val Lys
                20                  25                  30

Pro Gly Ala Ser Val Lys Met Ser Cys Lys Ala Ser Gly Tyr Thr Phe
            35                  40                  45

Thr Ser Tyr Val Ile His Trp Val Arg Gln Lys Pro Gly Gln Gly Leu
    50                  55                  60

Asp Trp Ile Gly Tyr Ile Asn Pro Tyr Asn Asp Gly Thr Asp Tyr Asp
65                  70                  75                  80

Glu Lys Phe Lys Gly Lys Ala Thr Leu Thr Ser Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Lys Asp Asn Tyr Ala Thr Gly Ala Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Phe Glu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Ser Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400
```

```
Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Leu His Glu Ala Leu His Ser His Tyr Thr Gln Lys Ser
            450                 455                 460

Leu Ser Leu Ser Pro Gly Lys Leu Glu Gly Gly Gly Ser Gly Gly
465                 470                 475                 480

Gly Gly Ser Gly Gly Gly Ser Gly Gln Val Leu Val Gln Ser
            485                 490                 495

Gly Gly Gly Leu Val Gln Pro Gly Gly Ser Leu Arg Leu Ser Cys Ala
            500                 505                 510

Ala Ser Ala Phe Asp Phe Ser Asp Tyr Glu Met Ser Trp Val Arg Gln
            515                 520                 525

Ala Pro Gly Lys Gly Leu Glu Trp Ile Gly Glu Ile Asn Asp Ser Gly
            530                 535                 540

Asn Thr Ile Tyr Asn Pro Ser Leu Lys Ser Arg Val Thr Ile Ser Arg
545                 550                 555                 560

Asp Asn Ser Lys Asn Thr Leu Tyr Leu Gln Met Asn Thr Leu Arg Ala
            565                 570                 575

Glu Asp Thr Ala Ile Tyr Tyr Cys Ala Ile Tyr Gly Gly Asn Ser Gly
            580                 585                 590

Gly Glu Tyr Trp Gly Gln Gly Thr Leu Val Thr Val Ser Ser
            595                 600                 605

<210> SEQ ID NO 2
<211> LENGTH: 473
<212> TYPE: PRT
<213> ORGANISM: Artificial Sequence
<220> FEATURE:
<223> OTHER INFORMATION: MV1 heavy chain

<400> SEQUENCE: 2

Met Glu Trp Ser Gly Val Phe Met Phe Leu Leu Ser Val Thr Ala Gly
1               5                   10                  15

Val His Ser Gln Val Gln Leu Gln Gln Ser Gly Pro Glu Val Val Lys
            20                  25                  30

Pro Gly Ala Ser Val Lys Met Ser Cys Lys Ala Ser Gly Tyr Thr Phe
            35                  40                  45

Thr Ser Tyr Val Ile His Trp Val Arg Gln Lys Pro Gly Gln Gly Leu
        50                  55                  60

Asp Trp Ile Gly Tyr Ile Asn Pro Tyr Asn Asp Gly Thr Asp Tyr Asp
65                  70                  75                  80

Glu Lys Phe Lys Gly Lys Ala Thr Leu Thr Ser Asp Thr Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Arg Glu Lys Asp Asn Tyr Ala Thr Gly Ala Trp Phe
            115                 120                 125

Ala Tyr Trp Gly Gln Gly Thr Leu Val Thr Val Ser Ala Ser Thr
            130                 135                 140

Lys Gly Pro Ser Val Phe Pro Leu Ala Pro Ser Ser Lys Ser Thr Ser
145                 150                 155                 160
```

```
Gly Gly Thr Ala Ala Leu Gly Cys Leu Val Lys Asp Tyr Phe Pro Glu
            165                 170                 175
Pro Val Thr Val Ser Trp Asn Ser Gly Ala Leu Thr Ser Gly Val His
        180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Phe Glu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Ser Ile Glu Lys Thr Ile Ser Lys Ala Lys Gly Gln Pro Arg
                355                 360                 365
Glu Pro Gln Val Tyr Thr Leu Pro Pro Ser Arg Asp Glu Leu Thr Lys
370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
                435                 440                 445
Cys Ser Val Leu His Glu Ala Leu His Ser His Tyr Thr Gln Lys Ser
                450                 455                 460
Leu Ser Leu Ser Pro Gly Lys Leu Glu
465                 470

<210> SEQ ID NO 3
<211> LENGTH: 16
<212> TYPE: PRT
<213> ORGANISM: Artificial Sequence
<220> FEATURE:
<223> OTHER INFORMATION: Synthetic linker

<400> SEQUENCE: 3

Gly Gly Gly Gly Ser Gly Gly Gly Ser Gly Gly Gly Ser Gly
1               5                   10                  15

<210> SEQ ID NO 4
<211> LENGTH: 117
<212> TYPE: PRT
<213> ORGANISM: Artificial Sequence
<220> FEATURE:
<223> OTHER INFORMATION: m36 variable heavy chain
```

```
<400> SEQUENCE: 4

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
            115

<210> SEQ ID NO 5
<211> LENGTH: 238
<212> TYPE: PRT
<213> ORGANISM: Artificial Sequence
<220> FEATURE:
<223> OTHER INFORMATION: MV1 light chain

<400> SEQUENCE: 5

Met Glu Trp Ser Gly Val Phe Ile Phe Leu Leu Ser Val Thr Ala Gly
1               5                   10                  15

Val His Ser Asp Ile Val Met Thr Gln Ser Pro Asp Ser Leu Ala Val
            20                  25                  30

Ser Leu Gly Glu Arg Val Thr Met Asn Cys Lys Ser Ser Gln Ser Leu
        35                  40                  45

Leu Tyr Ser Thr Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Val Tyr Tyr
            100                 105                 110

Cys Gln Gln Tyr Tyr Ser Tyr Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

```
225                 230                 235

<210> SEQ ID NO 6
<211> LENGTH: 19
<212> TYPE: PRT
<213> ORGANISM: Artificial Sequence
<220> FEATURE:
<223> OTHER INFORMATION: Leader sequence

<400> SEQUENCE: 6

Met Glu Trp Ser Gly Val Phe Ile Phe Leu Leu Ser Val Thr Ala Gly
1               5                   10                  15

Val His Ser

<210> SEQ ID NO 7
<211> LENGTH: 112
<212> TYPE: PRT
<213> ORGANISM: Artificial Sequence
<220> FEATURE:
<223> OTHER INFORMATION: MV1 variable light chain

<400> SEQUENCE: 7

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 8
<211> LENGTH: 107
<212> TYPE: PRT
<213> ORGANISM: Artificial Sequence
<220> FEATURE:
<223> OTHER INFORMATION: MV1 constant light chain

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 9
<211> LENGTH: 756
<212> TYPE: PRT
<213> ORGANISM: Artificial Sequence
<220> FEATURE:
<223> OTHER INFORMATION: a PG9-ibalizumab fusion polypeptide

<400> SEQUENCE: 9

Met Glu Trp Ser Gly Val Phe Met Phe Leu Leu Ser Val Thr Ala Gly
1               5                   10                  15

Val His Ser Gln Arg Leu Val Glu Ser Gly Gly Val Val Gln Pro
            20                  25                  30

Gly Ser Ser Leu Arg Leu Ser Cys Ala Ala Ser Gly Phe Asp Phe Ser
            35                  40                  45

Arg Gln Gly Met His Trp Val Arg Gln Ala Pro Gly Gln Gly Leu Glu
        50                  55                  60

Trp Val Ala Phe Ile Lys Tyr Asp Gly Ser Glu Lys Tyr His Ala Asp
65                  70                  75                  80

Ser Val Trp Gly Arg Leu Ser Ile Ser Arg Asp Asn Ser Lys Asp Thr
                85                  90                  95

Leu Tyr Leu Gln Met Asn Ser Leu Arg Val Glu Asp Thr Ala Thr Tyr
            100                 105                 110

Phe Cys Val Arg Glu Ala Gly Gly Pro Asp Tyr Arg Asn Gly Tyr Asn
        115                 120                 125

Tyr Tyr Asp Phe Tyr Asp Gly Tyr Tyr Asn Tyr His Tyr Met Asp Val
    130                 135                 140

Trp Gly Lys Gly Thr Thr Val Thr Val Ser Ser Gly Ile Leu Gly Ser
145                 150                 155                 160

Gly Gly Gly Gly Ser Gly Gly Gly Ser Gly Gly Gly Gly Ser Gln
                165                 170                 175

Ser Ala Leu Thr Gln Pro Ala Ser Val Ser Gly Ser Pro Gly Gln Ser
            180                 185                 190

Ile Thr Ile Ser Cys Asn Gly Thr Ser Asn Asp Val Gly Gly Tyr Glu
        195                 200                 205

Ser Val Ser Trp Tyr Gln Gln His Pro Gly Lys Ala Pro Lys Val Val
    210                 215                 220

Ile Tyr Asp Val Ser Lys Arg Pro Ser Gly Val Ser Asn Arg Phe Ser
225                 230                 235                 240

Gly Ser Lys Ser Gly Asn Thr Ala Ser Leu Thr Ile Ser Gly Leu Gln
                245                 250                 255

Ala Glu Asp Glu Gly Asp Tyr Tyr Cys Lys Ser Leu Thr Ser Thr Arg
            260                 265                 270

Arg Arg Val Phe Gly Thr Gly Thr Lys Leu Thr Val Leu Ser Gly Gly
        275                 280                 285

Gly Gly Ser Gly Gly Gly Gly Ser Gly Gly Gly Gly Ser Gln Val Gln
    290                 295                 300

Leu Gln Gln Ser Gly Pro Glu Val Val Lys Pro Gly Ala Ser Val Lys
305                 310                 315                 320

Met Ser Cys Lys Ala Ser Gly Tyr Thr Phe Thr Ser Tyr Val Ile His
                325                 330                 335

Trp Val Arg Gln Lys Pro Gly Gln Gly Leu Asp Trp Ile Gly Tyr Ile
            340                 345                 350

Asn Pro Tyr Asn Asp Gly Thr Asp Tyr Asp Glu Lys Phe Lys Gly Lys
        355                 360                 365

Ala Thr Leu Thr Ser Asp Thr Ser Thr Ser Thr Ala Tyr Met Glu Leu
    370                 375                 380
```

Ser Ser Leu Arg Ser Glu Asp Thr Ala Val Tyr Tyr Cys Ala Arg Glu
385                 390                 395                 400

Lys Asp Asn Tyr Ala Thr Gly Ala Trp Phe Ala Tyr Trp Gly Gln Gly
            405                 410                 415

Thr Leu Val Thr Val Ser Ser Ala Ser Thr Lys Gly Pro Ser Val Phe
            420                 425                 430

Pro Leu Ala Pro Ser Ser Arg Ser Thr Ser Glu Ser Thr Ala Ala Leu
            435                 440                 445

Gly Cys Leu Val Lys Asp Tyr Phe Pro Glu Pro Val Thr Val Ser Trp
    450                 455                 460

Asn Ser Gly Ser Leu Thr Ser Gly Val His Thr Phe Pro Ala Val Leu
465                 470                 475                 480

Gln Ser Ser Gly Leu Tyr Ser Leu Ser Ser Val Val Thr Val Pro Ser
                485                 490                 495

Ser Ser Leu Gly Thr Gln Thr Tyr Val Cys Asn Val Asn His Lys Pro
                500                 505                 510

Ser Asn Thr Lys Val Asp Lys Arg Val Glu Ile Lys Thr Cys Gly Gly
            515                 520                 525

Gly Ser Lys Pro Pro Thr Cys Pro Pro Cys Pro Ala Pro Glu Ala Ala
530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Asp Val Lys Phe Asn Trp Tyr Val Asn Gly Ala Glu
                580                 585                 590

Val His His Ala Gln Thr Lys Pro Arg Glu Thr Gln Tyr Asn Ser Thr
            595                 600                 605

Tyr Arg Val Val Ser Val Leu Thr Val Thr His Gln Asp Trp Leu Asn
610                 615                 620

Gly Lys Glu Tyr Thr Cys Lys Val Ser Asn Lys Ala Leu Pro Ala Ser
625                 630                 635                 640

Ile Gln Lys Thr Ile Ser Lys Asp Lys Gly Gln Pro Arg Glu Pro Gln
                645                 650                 655

Val Tyr Thr Leu Pro Pro Ser Arg Glu Glu Leu Thr Lys Asn Gln Val
                660                 665                 670

Ser Leu Thr Cys Pro Val Lys Gly Phe Tyr Pro Ser Asp Ile Val Val
            675                 680                 685

Glu Trp Glu Ser Ser Gly Gln Pro Glu Asn Thr Tyr Lys Thr Thr Pro
690                 695                 700

Pro Val Leu Asp Ser Asp Gly Ser Tyr Phe Leu Tyr Ser Lys Leu Thr
705                 710                 715                 720

Val Asp Lys Ser Arg Trp Gln Gln Gly Asn Val Phe Ser Cys Ser Val
                725                 730                 735

Met His Glu Ala Leu His Asn His Tyr Thr Gln Lys Ser Leu Ser Val
            740                 745                 750

Ser Pro Gly Lys
        755

<210> SEQ ID NO 10
<211> LENGTH: 19
<212> TYPE: PRT
<213> ORGANISM: Artificial Sequence
<220> FEATURE:
<223> OTHER INFORMATION: Signal peptide

```
<400> SEQUENCE: 10

Met Glu Trp Ser Gly Val Phe Met Phe Leu Leu Ser Val Thr Ala Gly
1               5                   10                  15

Val His Ser

<210> SEQ ID NO 11
<211> LENGTH: 136
<212> TYPE: PRT
<213> ORGANISM: Artificial Sequence
<220> FEATURE:
<223> OTHER INFORMATION: PG9 variable heavy chain

<400> SEQUENCE: 11

Gln Arg Leu Val Glu Ser Gly Gly Val Val Gln Pro Gly Ser Ser
1               5                   10                  15

Leu Arg Leu Ser Cys Ala Ala Ser Gly Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
        50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser
            130             135

<210> SEQ ID NO 12
<211> LENGTH: 20
<212> TYPE: PRT
<213> ORGANISM: Artificial Sequence
<220> FEATURE:
<223> OTHER INFORMATION: Synthetic linker

<400> SEQUENCE: 12

Gly Ile Leu Gly Ser Gly Gly Gly Ser Gly Gly Gly Ser Gly
1               5                   10                  15

Gly Gly Gly Ser
            20

<210> SEQ ID NO 13
<211> LENGTH: 110
<212> TYPE: PRT
<213> ORGANISM: Artificial Sequence
<220> FEATURE:
<223> OTHER INFORMATION: PG9 variable light chain

<400> SEQUENCE: 13

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
                20                  25                  30

Glu Ser Val Ser Trp Tyr Gln Gln His Pro Gly Lys Ala Pro Lys Val
            35                  40                  45
```

```
Val Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Lys Ser Leu Thr Ser Thr
                 85                  90                  95

Arg Arg Arg Val Phe Gly Thr Gly Thr Lys Leu Thr Val Leu
            100                 105                 110

<210> SEQ ID NO 14
<211> LENGTH: 16
<212> TYPE: PRT
<213> ORGANISM: Artificial Sequence
<220> FEATURE:
<223> OTHER INFORMATION: Synthetic linker

<400> SEQUENCE: 14

Ser Gly Gly Gly Gly Ser Gly Gly Gly Ser Gly Gly Gly Gly Ser
 1               5                  10                  15

<210> SEQ ID NO 15
<211> LENGTH: 122
<212> TYPE: PRT
<213> ORGANISM: Artificial Sequence
<220> FEATURE:
<223> OTHER INFORMATION: Ibalizumab variable heavy chain

<400> SEQUENCE: 15

Gln Val Gln Leu Gln Gln Ser Gly Pro Glu Val Val Lys Pro Gly Ala
 1               5                  10                  15

Ser Val Lys Met Ser Cys Lys Ala Ser Gly Tyr Thr Phe Thr Ser Tyr
             20                  25                  30

Val Ile His Trp Val Arg Gln Lys Pro Gly Gln Gly Leu Asp Trp Ile
         35                  40                  45

Gly Tyr Ile Asn Pro Tyr Asn Asp Gly Thr Asp Tyr Asp Glu Lys Phe
     50                  55                  60

Lys Gly Lys Ala Thr Leu Thr Ser Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Lys Asp Asn Tyr Ala Thr Gly Ala Trp Phe Ala Tyr Trp
            100                 105                 110

Gly Gln Gly Thr Leu Val Thr Val Ser Ser
        115                 120

<210> SEQ ID NO 16
<211> LENGTH: 333
<212> TYPE: PRT
<213> ORGANISM: Artificial Sequence
<220> FEATURE:
<223> OTHER INFORMATION: Ibalizumab Fc sequence

<400> SEQUENCE: 16

Ala Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ser Leu Thr Ser
         35                  40                  45

Gly Val His Thr Phe Pro Ala Val Leu Gln Ser Ser Gly Leu Tyr Ser
     50                  55                  60
```

```
Leu Ser Ser Val Val Thr Val Pro Ser Ser Leu Gly Thr Gln Thr
 65                  70                  75                  80

Tyr Val Cys Asn Val Asn His Lys Pro Ser Asn Thr Lys Val Asp Lys
                 85                  90                  95

Arg Val Glu Ile Lys Thr Cys Gly Gly Gly Ser Lys Pro Pro Thr Cys
            100                 105                 110

Pro Pro Cys Pro Ala Pro Glu Ala Ala Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser Gln Glu Asp Pro Asp Val Lys
145                 150                 155                 160

Phe Asn Trp Tyr Val Asn Gly Ala Glu Val His His Ala Gln Thr Lys
                165                 170                 175

Pro Arg Glu Thr Gln Tyr Asn Ser Thr Tyr Arg Val Val Ser Val Leu
            180                 185                 190

Thr Val Thr His Gln Asp Trp Leu Asn Gly Lys Glu Tyr Thr Cys Lys
        195                 200                 205

Val Ser Asn Lys Ala Leu Pro Ala Ser Ile Gln Lys Thr Ile Ser Lys
    210                 215                 220

Asp Lys Gly Gln Pro Arg Glu Pro Gln Val Tyr Thr Leu Pro Pro Ser
225                 230                 235                 240

Arg Glu Glu Leu Thr Lys Asn Gln Val Ser Leu Thr Cys Pro Val Lys
                245                 250                 255

Gly Phe Tyr Pro Ser Asp Ile Val Val Glu Trp Glu Ser Ser Gly Gln
            260                 265                 270

Pro Glu Asn Thr Tyr Lys Thr Thr Pro Pro Val Leu Asp Ser Asp Gly
        275                 280                 285

Ser Tyr Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Val Ser Pro Gly Lys
                325                 330

<210> SEQ ID NO 17
<211> LENGTH: 236
<212> TYPE: PRT
<213> ORGANISM: Artificial Sequence
<220> FEATURE:
<223> OTHER INFORMATION: Ibalizumab light chain

<400> SEQUENCE: 17

Met Arg Val Pro Ala Gln Leu Leu Gly Leu Leu Leu Leu Trp Leu Pro
1               5                   10                  15

Gly Ala Arg Gly Asp Ile Val Met Thr Gln Ser Pro Asp Ser Leu Ala
             20                  25                  30

Val Ser Leu Gly Glu Arg Val Thr Met Asn Cys Lys Ser Ser Gln Ser
         35                  40                  45

Leu Leu Tyr Ser Thr Asn Gln Lys Asn Tyr Leu Ala Trp Tyr Gln Gln
     50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                 85                  90                  95
```

-continued

```
Phe Thr Leu Thr Ile Ser Ser Val Gln Ala Glu Asp Val Ala Val Tyr
            100                 105                 110

Tyr Cys Gln Gln Tyr Tyr Ser Tyr Arg Thr Phe Gly Gly Gly Thr Lys
            115                 120                 125

Leu Glu Ile Lys Arg Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu
225                 230                 235

<210> SEQ ID NO 18
<211> LENGTH: 20
<212> TYPE: PRT
<213> ORGANISM: Artificial Sequence
<220> FEATURE:
<223> OTHER INFORMATION: Signal peptide

<400> SEQUENCE: 18

Met Arg Val Pro Ala Gln Leu Leu Gly Leu Leu Leu Leu Trp Leu Pro
1               5                   10                  15

Gly Ala Arg Gly
            20

<210> SEQ ID NO 19
<211> LENGTH: 113
<212> TYPE: PRT
<213> ORGANISM: Artificial Sequence
<220> FEATURE:
<223> OTHER INFORMATION: Ibalizumab variable light chain

<400> SEQUENCE: 19

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg

<210> SEQ ID NO 20
<211> LENGTH: 103
<212> TYPE: PRT
```

<213> ORGANISM: Artificial Sequence
<220> FEATURE:
<223> OTHER INFORMATION: Ibalizumab constant light chain

<400> SEQUENCE: 20

Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80

Val Tyr Ala Cys Glu Val Thr His Gln Gly Leu Ser Ser Pro Val Thr
                85                  90                  95

Lys Ser Phe Asn Arg Gly Glu
            100

<210> SEQ ID NO 21
<211> LENGTH: 720
<212> TYPE: PRT
<213> ORGANISM: Artificial Sequence
<220> FEATURE:
<223> OTHER INFORMATION: A VRC01-ibalizumab fusion polypeptide

<400> SEQUENCE: 21

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser Gly Gly Gly Ser Gly Gly
        115                 120                 125

Gly Gly Ser Gly Gly Gly Ser Gly Gly Gly Ser Glu Ile Val
    130                 135                 140

Leu Thr Gln Ser Pro Gly Thr Leu Ser Leu Ser Pro Gly Glu Thr Ala
145                 150                 155                 160

Ile Ile Ser Cys Arg Thr Ser Gln Tyr Gly Ser Leu Ala Trp Tyr Gln
                165                 170                 175

Gln Arg Pro Gly Gln Ala Pro Arg Leu Val Ile Tyr Ser Gly Ser Thr
            180                 185                 190

Arg Ala Ala Gly Ile Pro Asp Arg Phe Ser Gly Ser Arg Trp Gly Pro
        195                 200                 205

Asp Tyr Asn Leu Thr Ile Ser Asn Leu Glu Ser Gly Asp Phe Gly Val
    210                 215                 220

Tyr Tyr Cys Gln Gln Tyr Glu Phe Phe Gly Gln Gly Thr Lys Val Gln

```
                225                 230                 235                 240
Val Asp Ile Lys Arg Gly Gly Gly Ser Gly Gly Gly Gly Ser Gly
                    245                 250                 255
Gly Gly Gly Ser Gly Gly Gly Gly Ser Gln Val Gln Leu Gln Gln Ser
                260                 265                 270
Gly Pro Glu Val Val Lys Pro Gly Ala Ser Val Lys Met Ser Cys Lys
            275                 280                 285
Ala Ser Gly Tyr Thr Phe Thr Ser Tyr Val Ile His Trp Val Arg Gln
        290                 295                 300
Lys Pro Gly Gln Gly Leu Asp Trp Ile Gly Tyr Ile Asn Pro Tyr Asn
305                 310                 315                 320
Asp Gly Thr Asp Tyr Asp Glu Lys Phe Lys Gly Lys Ala Thr Leu Thr
                    325                 330                 335
Ser Asp Thr Ser Thr Ser Thr Ala Tyr Met Glu Leu Ser Ser Leu Arg
                340                 345                 350
Ser Glu Asp Thr Ala Val Tyr Tyr Cys Ala Arg Glu Lys Asp Asn Tyr
            355                 360                 365
Ala Thr Gly Ala Trp Phe Ala Tyr Trp Gly Gln Gly Thr Leu Val Thr
        370                 375                 380
Val Ser Ser Ala Ser Thr Lys Gly Pro Ser Val Phe Pro Leu Ala Pro
385                 390                 395                 400
Ser Ser Arg Ser Thr Ser Glu Ser Thr Ala Ala Leu Gly Cys Leu Val
                    405                 410                 415
Lys Asp Tyr Phe Pro Glu Pro Val Thr Val Ser Trp Asn Ser Gly Ser
                420                 425                 430
Leu Thr Ser Gly Val His Thr Phe Pro Ala Val Leu Gln Ser Ser Gly
            435                 440                 445
Leu Tyr Ser Leu Ser Ser Val Val Thr Val Pro Ser Ser Ser Leu Gly
        450                 455                 460
Thr Gln Thr Tyr Val Cys Asn Val Asn His Lys Pro Ser Asn Thr Lys
465                 470                 475                 480
Val Asp Lys Arg Val Glu Ile Lys Thr Cys Gly Gly Gly Ser Lys Pro
                    485                 490                 495
Pro Thr Cys Pro Pro Cys Pro Ala Pro Glu Ala Ala Gly Gly Pro Ser
                500                 505                 510
Val Phe Leu Phe Pro Pro Lys Pro Lys Asp Thr Leu Met Ile Ser Arg
            515                 520                 525
Thr Pro Glu Val Thr Cys Val Val Val Asp Val Ser Gln Glu Asp Pro
        530                 535                 540
Asp Val Lys Phe Asn Trp Tyr Val Asn Gly Ala Glu Val His His Ala
545                 550                 555                 560
Gln Thr Lys Pro Arg Glu Thr Gln Tyr Asn Ser Thr Tyr Arg Val Val
                    565                 570                 575
Ser Val Leu Thr Val Thr His Gln Asp Trp Leu Asn Gly Lys Glu Tyr
                580                 585                 590
Thr Cys Lys Val Ser Asn Lys Ala Leu Pro Ala Ser Ile Gln Lys Thr
            595                 600                 605
Ile Ser Lys Asp Lys Gly Gln Pro Arg Glu Pro Gln Val Tyr Thr Leu
        610                 615                 620
Pro Pro Ser Arg Glu Glu Leu Thr Lys Asn Gln Val Ser Leu Thr Cys
625                 630                 635                 640
Pro Val Lys Gly Phe Tyr Pro Ser Asp Ile Val Val Glu Trp Glu Ser
                    645                 650                 655
```

```
Ser Gly Gln Pro Glu Asn Thr Tyr Lys Thr Thr Pro Pro Val Leu Asp
            660                 665                 670

Ser Asp Gly Ser Tyr Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Val Ser Pro Gly Lys
705                 710                 715                 720

<210> SEQ ID NO 22
<211> LENGTH: 121
<212> TYPE: PRT
<213> ORGANISM: Artificial Sequence
<220> FEATURE:
<223> OTHER INFORMATION: VRC01 variable heavy chain

<400> SEQUENCE: 22

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 23
<211> LENGTH: 20
<212> TYPE: PRT
<213> ORGANISM: Artificial Sequence
<220> FEATURE:
<223> OTHER INFORMATION: Synthetic linker

<400> SEQUENCE: 23

Gly Gly Gly Gly Ser Gly Gly Gly Ser Gly Gly Gly Ser
1               5                   10                  15

Gly Gly Gly Ser
            20

<210> SEQ ID NO 24
<211> LENGTH: 104
<212> TYPE: PRT
<213> ORGANISM: Artificial Sequence
<220> FEATURE:
<223> OTHER INFORMATION: VRC01 variable light chain

<400> SEQUENCE: 24

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45
```

-continued

```
Gly Ser Thr Arg Ala Ala Gly Ile Pro Asp Arg Phe Ser Gly Ser Arg
        50                  55                  60

Trp Gly Pro Asp Tyr Asn Leu Thr Ile Ser Asn Leu Glu Ser Gly Asp
 65                  70                  75                  80

Phe Gly Val Tyr Tyr Cys Gln Gln Tyr Glu Phe Gly Gln Gly Thr
                85                  90                  95

Lys Val Gln Val Asp Ile Lys Arg
            100

<210> SEQ ID NO 25
<211> LENGTH: 219
<212> TYPE: PRT
<213> ORGANISM: Artificial Sequence
<220> FEATURE:
<223> OTHER INFORMATION: Rhesus Ibalizumab light chain

<400> SEQUENCE: 25

Asp Ile Val Met Thr Gln Ser Pro Ser Ser Leu Ser Val Ser Leu Gly
 1               5                  10                  15

Glu Arg Val Thr Met Thr Cys Lys Ser Ser Gln Ser Leu Leu Tyr Ser
                20                  25                  30

Thr Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Val Gln Pro Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Ala Val Ala Ala Pro Ser Val Phe Ile Phe Pro Pro Ser Glu Asp
        115                 120                 125

Gln Val Lys Ser Gly Thr Val Ser Val Val Cys Leu Leu Asn Asn Phe
    130                 135                 140

Tyr Pro Arg Glu Ala Ser Val Lys Trp Lys Val Asp Gly Val Leu Lys
145                 150                 155                 160

Thr Gly Asn Ser Gln Glu Ser Val Thr Glu Gln Asp Ser Lys Asp Asn
                165                 170                 175

Thr Tyr Ser Leu Ser Ser Thr Leu Thr Leu Ser Ser Thr Asp Tyr Gln
            180                 185                 190

Ser His Asn Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 455
<212> TYPE: PRT
<213> ORGANISM: Artificial Sequence
<220> FEATURE:
<223> OTHER INFORMATION: Rhesus Ibalizumab heavy chain

<400> SEQUENCE: 26

Glu Val Gln Leu Gln Gln Ser Gly Ala Glu Val Val Lys Pro Gly Ala
 1               5                  10                  15

Ser Val Lys Met Ser Cys Lys Ala Ser Gly Tyr Thr Phe Thr Ser Tyr
                20                  25                  30
```

```
Val Ile His Trp Val Arg Gln Lys Pro Gly Gln Gly Leu Asp Trp Ile
         35                  40                  45
Gly Tyr Ile Asn Pro Tyr Asn Asp Gly Thr Asp Tyr Asp Glu Lys Phe
         50                  55                  60
Lys Gly Lys Ala Thr Leu Thr Ser Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Lys Asp Asn Tyr Ala Thr Gly Ala Trp Phe Ala Tyr Trp
                100                 105                 110
Gly Gln Gly Val Leu Val Thr Val Ser Ser Ala Ser Thr Lys Gly Pro
            115                 120                 125
Ser Val Phe Pro Leu Ala Pro Ser Ser Arg Ser Thr Ser Glu Ser Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ser Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Val Cys Asn Val Asn
        195                 200                 205
His Lys Pro Ser Asn Thr Lys Val Asp Lys Arg Val Glu Ile Lys Thr
    210                 215                 220
Cys Gly Gly Gly Ser Lys Pro Pro Thr Cys Pro Pro Cys Pro Ala Pro
225                 230                 235                 240
Glu Ala Ala Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser Gln Glu Asp Pro Asp Val Lys Phe Asn Trp Tyr Val Asn
        275                 280                 285
Gly Ala Glu Val His His Ala Gln Thr Lys Pro Arg Glu Thr Gln Tyr
    290                 295                 300
Asn Ser Thr Tyr Arg Val Val Ser Val Leu Thr Val Thr His Gln Asp
305                 310                 315                 320
Trp Leu Asn Gly Lys Glu Tyr Thr Cys Lys Val Ser Asn Lys Ala Leu
                325                 330                 335
Pro Ala Ser Ile Gln Lys Thr Ile Ser Lys Asp Lys Gly Gln Pro Arg
            340                 345                 350
Glu Pro Gln Val Tyr Thr Leu Pro Pro Ser Arg Glu Glu Leu Thr Lys
        355                 360                 365
Asn Gln Val Ser Leu Thr Cys Leu Val Lys Gly Phe Tyr Pro Ser Asp
    370                 375                 380
Ile Val Val Glu Trp Glu Ser Ser Gly Gln Pro Glu Asn Thr Tyr Lys
385                 390                 395                 400
Thr Thr Pro Pro Val Leu Asp Ser Asp Gly Ser Tyr Phe Leu Tyr Ser
                405                 410                 415
Lys Leu Thr Val Asp Lys Ser Arg Trp Gln Gln Gly Asn Val Phe Ser
            420                 425                 430
Cys Ser Val Leu His Glu Ala Leu His Ser His Tyr Thr Gln Lys Ser
        435                 440                 445
Leu Ser Val Ser Pro Gly Lys
```

```
                 450                 455

<210> SEQ ID NO 27
<211> LENGTH: 267
<212> TYPE: PRT
<213> ORGANISM: Artificial Sequence
<220> FEATURE:
<223> OTHER INFORMATION: Rhesus PG9 scFv

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Gln
            20                  25                  30

Gly Met His Trp Val Arg Gln Ala Pro Gly Lys Gly Leu Glu Trp Val
        35                  40                  45

Ala Phe Ile Lys Tyr Asp Gly Ser Glu Lys Tyr His Ala Asp Ser Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Gly Pro Asp Tyr Arg Asn Gly Tyr Asn Tyr Tyr
            100                 105                 110

Asp Phe Tyr Asp Gly Tyr Tyr Asn Tyr His Tyr Met Asp Val Trp Gly
        115                 120                 125

Lys Gly Thr Thr Val Thr Val Ser Ser Gly Ile Leu Gly Ser Gly Gly
    130                 135                 140

Gly Gly Ser Gly Gly Gly Ser Gly Gly Gly Ser Gln Ser Ala
145                 150                 155                 160

Leu Thr Gln Pro Pro Ser Val Ser Gly Ser Pro Gly Gln Ser Val Thr
                165                 170                 175

Ile Ser Cys Asn Gly Thr Ser Asn Asp Val Gly Gly Tyr Glu Ser Val
            180                 185                 190

Ser Trp Tyr Gln Gln His Pro Gly Lys Ala Pro Lys Leu Val Ile Tyr
        195                 200                 205

Asp Val Ser Lys Arg Pro Ser Gly Val Ser Asp Arg Phe Ser Gly Ser
    210                 215                 220

Lys Ser Gly Asn Thr Ala Ser Leu Thr Ile Ser Gly Leu Gln Ala Glu
225                 230                 235                 240

Asp Glu Ala Asp Tyr Tyr Cys Lys Ser Leu Thr Ser Thr Arg Arg Arg
                245                 250                 255

Val Phe Gly Thr Gly Thr Lys Leu Thr Val Leu
            260                 265

<210> SEQ ID NO 28
<211> LENGTH: 137
<212> TYPE: PRT
<213> ORGANISM: Artificial Sequence
<220> FEATURE:
<223> OTHER INFORMATION: Heavy chain of Rhesus PG9 scFv

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Gln
            20                  25                  30

Gly Met His Trp Val Arg Gln Ala Pro Gly Lys Gly Leu Glu Trp Val
```

-continued

```
                35                  40                  45
Ala Phe Ile Lys Tyr Asp Gly Ser Glu Lys Tyr His Ala Asp Ser Val
 50                  55                  60

Trp Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Gly Gly Pro Asp Tyr Arg Asn Gly Tyr Asn Tyr Tyr
                100                 105                 110

Asp Phe Tyr Asp Gly Tyr Tyr Asn Tyr His Tyr Met Asp Val Trp Gly
                115                 120                 125

Lys Gly Thr Thr Val Thr Val Ser Ser
130                 135

<210> SEQ ID NO 29
<211> LENGTH: 110
<212> TYPE: PRT
<213> ORGANISM: Artificial Sequence
<220> FEATURE:
<223> OTHER INFORMATION: Light chain of Rhesus PG9 scFv

<400> SEQUENCE: 29

Gln Ser Ala Leu Thr Gln Pro Pro Ser Val Ser Gly Ser Pro Gly Gln
 1               5                  10                  15

Ser Val Thr Ile Ser Cys Asn Gly Thr Ser Asn Asp Val Gly Gly Tyr
                20                  25                  30

Glu Ser Val Ser Trp Tyr Gln Gln His Pro Gly Lys Ala Pro Lys Leu
            35                  40                  45

Val Ile Tyr Asp Val Ser Lys Arg Pro Ser Gly Val Ser Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Lys Ser Leu Thr Ser Thr
                 85                  90                  95

Arg Arg Arg Val Phe Gly Thr Gly Thr Lys Leu Thr Val Leu
                100                 105                 110

<210> SEQ ID NO 30
<211> LENGTH: 606
<212> TYPE: PRT
<213> ORGANISM: Artificial Sequence
<220> FEATURE:
<223> OTHER INFORMATION: iMab-m36 heavy chain containing the LALA+FcRn
      mutations

<400> SEQUENCE: 30

Met Glu Trp Ser Gly Val Phe Met Phe Leu Leu Ser Val Thr Ala Gly
 1               5                  10                  15

Val His Ser Gln Val Gln Leu Gln Gln Ser Gly Pro Glu Val Val Lys
                20                  25                  30

Pro Gly Ala Ser Val Lys Met Ser Cys Lys Ala Ser Gly Tyr Thr Phe
            35                  40                  45

Thr Ser Tyr Val Ile His Trp Val Arg Gln Lys Pro Gly Gln Gly Leu
 50                  55                  60

Asp Trp Ile Gly Tyr Ile Asn Pro Tyr Asn Asp Gly Thr Asp Tyr Asp
 65                  70                  75                  80

Glu Lys Phe Lys Gly Lys Ala Thr Leu Thr Ser Asp Thr Ser Thr Ser
                 85                  90                  95
```

```
Thr Ala Tyr Met Glu Leu Ser Ser Leu Arg Ser Glu Asp Thr Ala Val
            100                 105                 110
Tyr Tyr Cys Ala Arg Glu Lys Asp Asn Tyr Ala Thr Gly Ala Trp Phe
        115                 120                 125
Ala Tyr Trp Gly Gln Gly Thr Leu Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Phe Glu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Ser Ile Glu Lys Thr Ile Ser Lys Ala Lys Gly Gln Pro Arg
        355                 360                 365
Glu Pro Gln Val Tyr Thr Leu Pro Pro Ser Arg Asp Glu Leu Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Leu His Glu Ala Leu His Ser His Tyr Thr Gln Lys Ser
    450                 455                 460
Leu Ser Leu Ser Pro Gly Lys Leu Glu Gly Gly Gly Ser Gly Gly
465                 470                 475                 480
Gly Gly Ser Gly Gly Gly Ser Gly Gln Val Gln Leu Val Gln Ser
                485                 490                 495
Gly Gly Gly Leu Val Gln Pro Gly Gly Ser Leu Arg Leu Ser Cys Ala
            500                 505                 510
Ala Ser Ala Phe Asp Phe Ser Asp Tyr Glu Met Ser Trp Val Arg Gln
        515                 520                 525
```

```
Ala Pro Gly Lys Gly Leu Glu Trp Ile Gly Glu Ile Asn Asp Ser Gly
            530                 535                 540

Asn Thr Ile Tyr Asn Pro Ser Leu Lys Ser Arg Val Thr Ile Ser Arg
545                 550                 555                 560

Asp Asn Ser Lys Asn Thr Leu Tyr Leu Gln Met Asn Thr Leu Arg Ala
                565                 570                 575

Glu Asp Thr Ala Ile Tyr Tyr Cys Ala Ile Tyr Gly Gly Asn Ser Gly
            580                 585                 590

Gly Glu Tyr Trp Gly Gln Gly Thr Leu Val Thr Val Ser Ser
            595                 600                 605

<210> SEQ ID NO 31
<211> LENGTH: 452
<212> TYPE: PRT
<213> ORGANISM: Artificial Sequence
<220> FEATURE:
<223> OTHER INFORMATION: iMab heavy chain with LALA and FcRn mutations

<400> SEQUENCE: 31

Gln Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Arg Gln Lys Pro Gly Gln Gly Leu Asp Trp Ile
        35                  40                  45

Gly Tyr Ile Asn Pro Tyr Asn Asp Gly Thr Asp Tyr Asp Glu Lys Phe
    50                  55                  60

Lys Gly Lys Ala Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Asp Asn Tyr Ala Thr Gly Ala Trp Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Leu His Glu Ala Leu His Ser His Tyr Thr Gln Lys Ser Leu Ser Leu
        435                 440                 445

Ser Pro Gly Lys
    450

<210> SEQ ID NO 32
<211> LENGTH: 18
<212> TYPE: PRT
<213> ORGANISM: Artificial Sequence
<220> FEATURE:
<223> OTHER INFORMATION: Synthetic linker

<400> SEQUENCE: 32

Leu Glu Gly Gly Gly Gly Ser Gly Gly Gly Gly Ser Gly Gly Gly Gly
1               5                   10                  15

Ser Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Gly Gly Gly Gly Ser
1               5

<210> SEQ ID NO 34
<211> LENGTH: 458
<212> TYPE: PRT
<213> ORGANISM: Homo sapiens

<400> SEQUENCE: 34

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60
```

```
Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Trp Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 35
<211> LENGTH: 854
<212> TYPE: PRT
```

<213> ORGANISM: Homo sapiens

<400> SEQUENCE: 35

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asp Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Asp Lys Val Gln Lys Glu Tyr Ala Phe Phe
                165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys

```
                     405                 410                 415
Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
        435                 440                 445

Gly Leu Leu Leu Thr Arg Asp Gly Asn Asn Asn Gly Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
        515                 520                 525

Gly Ala Ala Ser Met Thr Leu Thr Val Gln Ala Arg Gln Leu Leu Ser
    530                 535                 540

Asp Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Ile Trp Asn Asn Met
    610                 615                 620

Thr Trp Met Glu Trp Asp Arg Glu Ile Asn Asn Tyr Thr Ser Leu Ile
625                 630                 635                 640

His Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Leu Phe Ile Met Ile Val Gly
        675                 680                 685

Gly Leu Val Gly Leu Arg Ile Val Phe Ala Val Leu Ser Ile Val Asn
    690                 695                 700

Arg Val Arg Gln Gly Tyr Ser Pro Leu Ser Phe Gln Thr His Leu Pro
705                 710                 715                 720

Ile Pro Arg Gly Pro Asp Arg Pro Glu Gly Ile Glu Glu Gly Gly
                725                 730                 735

Glu Arg Gly Arg Asp Arg Ser Ile Arg Leu Val Asn Gly Ser Leu Ala
            740                 745                 750

Leu Ile Trp Asp Asp Leu Arg Ser Leu Cys Leu Phe Ser Tyr His Arg
        755                 760                 765

Leu Arg Asp Leu Leu Leu Ile Val Thr Arg Ile Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Asn Leu Leu Asn Ala Thr
                805                 810                 815

Ala Ile Ala Val Ala Glu Gly Thr Asp Arg Val Ile Glu Val Leu Gln
            820                 825                 830
```

```
Ala Ala Tyr Arg Ala Ile Arg His Ile Pro Arg Arg Ile Arg Gln Gly
        835                 840                 845

Leu Glu Arg Ile Leu Leu
    850

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Thr Ser Tyr Val Ile His
1               5

<210> SEQ ID NO 37
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 37

Thr Ser Gln Thr Ile His
1               5

<210> SEQ ID NO 38
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 38

Thr Ser Gln Thr Leu His
1               5

<210> SEQ ID NO 39
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 39

Thr Ala Gln Thr Ile His
1               5

<210> SEQ ID NO 40
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 40

Thr Ala Gln Thr Leu His
1               5

<210> SEQ ID NO 41
<211> LENGTH: 6
<212> TYPE: PRT
<213> ORGANISM: Artificial Sequence
```

```
<220> FEATURE:
<223> OTHER INFORMATION: Peptide sequence from affinity maturation
      variant

<400> SEQUENCE: 41

Thr Glu Gln Thr Leu His
1               5

<210> SEQ ID NO 42
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 42

Thr Asp Gln Thr Leu His
1               5

<210> SEQ ID NO 43
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 43

Thr Asp Gln Thr Met His
1               5

<210> SEQ ID NO 44
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 44

Thr Gly Gln Thr Leu His
1               5

<210> SEQ ID NO 45
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 45

Thr Asn Gln Thr Leu His
1               5

<210> SEQ ID NO 46
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 46

Thr Asn Gln Val Ile His
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 47

Thr Asp Tyr Thr Phe His
1               5

<210> SEQ ID NO 48
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 48

Thr Glu Tyr Thr Phe His
1               5

<210> SEQ ID NO 49
<211> LENGTH: 6
<212> TYPE: PRT
<213> ORGANISM: Artificial Sequence
<220> FEATURE:
<223> OTHER INFORMATION: Peptide sequence from affinity maturation
      variant

<400> SEQUENCE: 49

Thr Asp Tyr Thr Ile His
1               5

<210> SEQ ID NO 50
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 50

Glu Gln Thr Leu His
1               5

<210> SEQ ID NO 51
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 51

Ala Gln Thr Leu His
1               5

<210> SEQ ID NO 52
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 52
```

Glu Tyr Thr Phe His
1               5

<210> SEQ ID NO 53
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 53

Ser Gln Thr Leu His
1               5

<210> SEQ ID NO 54
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 54

Asp Tyr Thr Phe His
1               5

<210> SEQ ID NO 55
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 55

Asp Gln Thr Leu His
1               5

<210> SEQ ID NO 56
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 56

Ser Gln Thr Ile His
1               5

<210> SEQ ID NO 57
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 57

Asp Tyr Thr Ile His
1               5

<210> SEQ ID NO 58
<211> LENGTH: 5
<212> TYPE: PRT
<213> ORGANISM: Artificial Sequence
<220> FEATURE:
<223> OTHER INFORMATION: Peptide sequence of CDR-H1 of iMab

```
<400> SEQUENCE: 58

Ser Tyr Val Ile His
1               5

<210> SEQ ID NO 59
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 59

Ser Arg Val Leu Ser
1               5

<210> SEQ ID NO 60
<211> LENGTH: 14
<212> TYPE: PRT
<213> ORGANISM: Artificial Sequence
<220> FEATURE:
<223> OTHER INFORMATION: Peptide sequence of CDR-H3 of iMab

<400> SEQUENCE: 60

Ala Arg Glu Lys Asp Asn Tyr Ala Thr Gly Ala Trp Phe Ala
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Peptide sequence of CDR-H3 of iMab

<400> SEQUENCE: 61

Ala Arg Glu Lys Asp Asn Tyr Ala Val Pro Gly Trp Phe Ala
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Peptide sequence from affinity maturation
      variant

<400> SEQUENCE: 62

Ala Arg Glu Lys Asp Ser Leu Thr Thr Gly Ala Trp Phe Ala
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Peptide sequence from affinity maturation
      variant

<400> SEQUENCE: 63

Val Arg Glu Lys Asp Ser Phe Ala Thr Gly Ala Trp Phe Ala
1               5                   10

<210> SEQ ID NO 64
<211> LENGTH: 14
<212> TYPE: PRT
<213> ORGANISM: Artificial Sequence
<220> FEATURE:
```

```
<223> OTHER INFORMATION: Peptide sequence from affinity maturation
      variant

<400> SEQUENCE: 64

Ala Arg Gln Ala Ala Asn Tyr Ala Thr Gly Ala Trp Phe Ala
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Peptide sequence from affinity maturation
      variant

<400> SEQUENCE: 65

Glu Tyr Thr Ile His
1               5

<210> SEQ ID NO 66
<211> LENGTH: 14
<212> TYPE: PRT
<213> ORGANISM: Artificial Sequence
<220> FEATURE:
<223> OTHER INFORMATION: Peptide sequence from affinity maturation
      variant

<400> SEQUENCE: 66

Ala Arg Ala Lys Asp Asn Tyr Ala Thr Gly Ala Trp Phe Ala
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic Construct

<400> SEQUENCE: 67

Glu Lys Asp Asn Tyr Ala Thr Gly Ala Trp Phe Ala Tyr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic Construct

<400> SEQUENCE: 68

Ala Lys Asp Asn Ala Ala Thr Gly Ala Trp Phe Ala Tyr
1               5                   10
```